US009962336B2

(12) United States Patent
Singh et al.

(10) Patent No.: US 9,962,336 B2
(45) Date of Patent: *May 8, 2018

(54) EXTENDED RELEASE SUSPENSION COMPOSITIONS

(71) Applicant: SUN PHARMACEUTICAL INDUSTRIES LIMITED, Mumbai, Maharashtra (IN)

(72) Inventors: Romi Barat Singh, Benares (IN); Ashish Kumar, Jhajjar (IN); Rajesh Srikrishan Shear, Gurgaon (IN); Satish Kumar Jain, Bilaspur (IN); Paras P. Jain, Amravati (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/148,069

(22) Filed: May 6, 2016

(65) Prior Publication Data

US 2016/0271070 A1 Sep. 22, 2016

Related U.S. Application Data

(63) Continuation-in-part of application No. 15/133,826, filed on Apr. 20, 2016, which is a continuation of application No. PCT/IB2015/053209, filed on May 1, 2015.

(30) Foreign Application Priority Data

May 1, 2014 (IN) .......................... 1183/DEL/2014

(51) Int. Cl.
| | |
|---|---|
| *A61K 9/00* | (2006.01) |
| *A61K 9/10* | (2006.01) |
| *A61K 9/50* | (2006.01) |
| *A61K 31/155* | (2006.01) |
| *A61K 31/165* | (2006.01) |
| *A61K 31/522* | (2006.01) |
| *A61K 31/43* | (2006.01) |
| *A61K 31/4439* | (2006.01) |
| *A61K 9/14* | (2006.01) |

(52) U.S. Cl.
CPC .......... *A61K 9/5078* (2013.01); *A61K 9/0095* (2013.01); *A61K 9/10* (2013.01); *A61K 9/145* (2013.01); *A61K 9/5026* (2013.01); *A61K 9/5031* (2013.01); *A61K 9/5042* (2013.01); *A61K 9/5047* (2013.01); *A61K 9/5084* (2013.01); *A61K 9/5089* (2013.01); *A61K 31/155* (2013.01); *A61K 31/165* (2013.01); *A61K 31/43* (2013.01); *A61K 31/4439* (2013.01); *A61K 31/522* (2013.01)

(58) Field of Classification Search
CPC ................... A61K 9/5047; A61K 9/10
See application file for complete search history.

(56) References Cited

U.S. PATENT DOCUMENTS

| | | | |
|---|---|---|---|
| 3,156,369 A | 11/1964 | Bowes et al. ...................... 215/6 |
| 3,603,469 A | 9/1971 | Magni ............................... 215/6 |
| 3,632,645 A | 1/1972 | Bream et al. .................. 260/558 |
| 3,840,136 A | 10/1974 | Lanfranconi et al. ............ 215/6 |
| 4,024,952 A | 5/1977 | Leitz |
| 4,982,875 A | 1/1991 | Pozzi et al. ...................... 222/83 |
| 5,058,770 A | 10/1991 | Herold et al. ................... 222/80 |
| 5,273,760 A | 12/1993 | Oshlack et al. |
| 5,419,445 A | 5/1995 | Kaesemeyer |
| 5,431,915 A | 7/1995 | Harvey et al. ................. 424/439 |
| 5,460,828 A * | 10/1995 | Santus ................. A61K 9/1694 424/470 |
| 5,472,712 A | 12/1995 | Oshlack et al. |
| 5,854,290 A | 12/1998 | Arnsten et al. ............... 514/617 |
| 5,955,106 A | 9/1999 | Moeckel et al. |
| 6,148,996 A | 11/2000 | Morini .......................... 206/222 |
| 6,156,340 A | 12/2000 | Adeyeye et al. ............. 424/463 |
| 6,287,599 B1 | 9/2001 | Burnside et al. ............. 424/468 |
| 6,676,966 B1 | 1/2004 | Odidi et al. |
| 6,811,794 B2 | 11/2004 | Burnside et al. ............. 424/468 |
| 6,890,957 B2 | 5/2005 | Chandran et al. |
| 7,214,387 B2 | 5/2007 | Sanghvi et al. |
| 7,906,145 B2 | 3/2011 | Castan et al. ................. 424/489 |
| 8,002,734 B2 | 8/2011 | Bassarab et al. ............... 604/82 |
| 8,197,850 B2 | 6/2012 | Castan et al. |

(Continued)

FOREIGN PATENT DOCUMENTS

| | | | |
|---|---|---|---|
| EP | 0 601 508 B1 | 3/1999 | |
| EP | 1 140 027 | 10/2005 | ............... A61K 9/16 |

(Continued)

OTHER PUBLICATIONS

Kristine, "EKG Results/Tenex", Dr. Mom's Spot (Mar. 26, 2010) Available: http://drmomsspot.blogspot.com/2010/03/ekg-results-tenex.html.
Co-pending PCT Application No. PCT/IB2015/053209 filed May 1, 2015.
International Search Report and Written Opinion for International Application No. PCT/IB2015/053209, issued by PCT dated Aug. 14, 2015.
International Preliminary Report on Patentability for International Application No. PCT/IB2015/053209, issued by PCT dated Nov. 10, 2016.
Co-pending U.S. Appl. No. 15/133,826, filed Apr. 20, 2016.
Office Action for U.S. Appl. No. 15/133,826, issued by USPTO dated Jul. 28, 2016.

(Continued)

*Primary Examiner* — Gina C Justice
(74) *Attorney, Agent, or Firm* — Liang, Frank & King, LLP; Stanley D. Liang

(57) ABSTRACT

The present invention relates to a method for preparing a stable extended release suspension composition comprising multiple coated cores of an active ingredient by using a suspension base, wherein the suspension base ensures substantially similar in-vitro dissolution release profile of the active ingredient upon storage of the suspension compositions for at least seven days.

10 Claims, 3 Drawing Sheets

(56) References Cited

U.S. PATENT DOCUMENTS

| | | | |
|---|---|---|---|
| 8,297,456 B1 | 10/2012 | Anderson | |
| 8,318,210 B2 | 11/2012 | Tengler et al. | |
| 8,453,833 B2 | 6/2013 | Porter | |
| 8,491,935 B2 | 7/2013 | Mehta et al. | |
| 8,541,018 B2 | 9/2013 | Radke et al. | 424/439 |
| 8,960,424 B1 | 2/2015 | Anderson | |
| 9,132,950 B1 | 9/2015 | Anderson et al. | |
| 2001/0032643 A1 | 10/2001 | Hochrainer et al. | 128/200.21 |
| 2003/0171407 A1 | 9/2003 | Freese et al. | |
| 2003/0199846 A1 | 10/2003 | Fowles et al. | 604/403 |
| 2004/0062800 A1 | 4/2004 | Burnside et al. | 424/468 |
| 2004/0062802 A1 | 4/2004 | Hermelin | 424/468 |
| 2004/0109891 A1 | 6/2004 | Sanghvi et al. | |
| 2007/0193894 A1 | 8/2007 | MacKen et al. | 206/219 |
| 2008/0008765 A1* | 1/2008 | Schwarz | A61K 9/0095 424/493 |
| 2008/0095855 A1 | 4/2008 | Schwarz | |
| 2008/0118570 A1 | 5/2008 | Liu et al. | 424/490 |
| 2008/0124432 A1 | 5/2008 | Ma | |
| 2008/0202950 A1 | 8/2008 | Anderson | 206/219 |
| 2008/0314775 A1 | 12/2008 | Owoc | |
| 2009/0123538 A1 | 5/2009 | Alani et al. | |
| 2009/0142378 A1 | 6/2009 | Frisbee | |
| 2009/0176691 A1 | 7/2009 | Bennis et al. | |
| 2009/0325938 A1 | 12/2009 | Lichter et al. | |
| 2010/0092562 A1 | 4/2010 | Hollenbeck et al. | 424/488 |
| 2010/0282624 A1 | 11/2010 | Paganuzzi | |
| 2010/0330150 A1 | 12/2010 | Venkatesh et al. | |
| 2011/0268808 A1 | 11/2011 | Jain et al. | |
| 2011/0313046 A1 | 12/2011 | Ermer | 514/617 |
| 2012/0178666 A1 | 7/2012 | Franklin et al. | 514/1.3 |
| 2012/0220930 A1 | 8/2012 | Griffiths et al. | 604/89 |
| 2013/0109659 A1 | 5/2013 | Soler Ranzani et al. | |
| 2014/0050796 A1 | 2/2014 | Tengler et al. | 424/494 |
| 2014/0309271 A1 | 10/2014 | Price | |
| 2014/0319141 A1 | 10/2014 | Stratis et al. | |
| 2015/0021214 A1 | 1/2015 | Besic et al. | |

FOREIGN PATENT DOCUMENTS

| | | | |
|---|---|---|---|
| EP | 1 140 027 B1 | 12/2005 | |
| FR | 2 897 267 A1 | 8/2017 | |
| WO | 00 38655 A1 | 7/2000 | |
| WO | WO 00/38655 | 7/2000 | A61K 9/16 |
| WO | WO 2006/030297 | 3/2003 | A61K 9/16 |
| WO | WO 2004 012715 A1 | 2/2004 | |
| WO | WO 2006 086856 A1 | 7/2008 | |
| WO | WO 2008/122993 | 10/2008 | A61K 9/16 |
| WO | WO 2010 045656 A3 | 4/2010 | |
| WO | WO 2011/077451 | 6/2011 | A61K 9/28 |
| WO | WO 2011/107855 | 9/2011 | A61K 9/50 |
| WO | 2011 150506 A1 | 12/2011 | |
| WO | WO 2011/150506 | 12/2011 | A61K 9/48 |
| WO | WO 2012/063257 | 5/2012 | A61K 47/30 |
| WO | WO 2014/174119 | 10/2014 | A61K 31/155 |

OTHER PUBLICATIONS

Co-pending PCT Application No. PCT/IB2016/052604 filed May 6, 2016.
International Search Report and Written Opinion for International Application No. PCT/IB2016/052604, issued by PCT dated Aug. 31, 2016.
Co-pending PCT Application No. PCT/IB2016/052607 filed May 6, 2016.
International Search Report and Written Opinion for International Application No. PCT/IB2016/052607, issued by PCT dated Sep. 2, 2016.
Co-pending U.S. Appl. No. 15/148,131, filed May 6, 2016.
Office Action for U.S. Appl. No. 15/148,131, issued by USPTO dated Oct. 7, 2016.
Co-pending PCT Application No. PCT/IB2016/052485 filed May 2, 2016.
International Search Report and Written Opinion for International Application No. PCT/IB2016/052485, issued by PCT dated Aug. 31, 2016.
Co-pending U.S. Appl. No. 15/144,026, filed May 2, 2016.
Office Action for U.S. Appl. No. 15/144,026, issued by USPTO dated Oct. 12, 2016.
Co-pending PCT Application No. PCT/IB2015/055780 filed Jul. 30, 2015.
International Search Report and Written Opinion for International Application No. PCT/IB2015/055780, issued by PCT dated Dec. 7, 2015.
Co-pending PCT Application No. PCT/IB2016/052486 filed May 2, 2016.
International Search Report and Written Opinion for International Application No. PCT/162016/052486, issued by PCT dated Sep. 9, 2016.
Co-pending U.S. Appl. No. 15/144,058, filed May 2, 2016.
Co-pending U.S. Appl. No. 15/352,993, filed Nov. 16, 2016.
Steeman, 2009. Innovative dispensing bottle caps for sensitive vitamins [online]. Best in Packaging. Available from: http://bestinpackaging.com/2009/05/29/innovative-dispensing-bottle-caps-for-sensitive-vitamins/.
Lopez-Liuchi et al., "Therapy for type 2 diabetes: where do we stand after the UK Prospective Diabetes Study?," European Journal of Endocrinology, 140:4-6 (1999).
Murtaza,"Ethylcellulose Microparticles: A Review," Drug Research, 69(1):11-22 (2012).
Co-pending PCT Application No. PCT/IB2015/053207 filed May 1, 2015, published as WO 2015/166472 on Nov. 5, 2015.
International Preliminary Report on Patentability for International Application No. PCT/IB2015/053207, issued by WIPO dated Mar. 16, 2016.
Co-pending U.S. Appl. No. 15/133,773, filed Apr. 20, 2016, published as U.S. 2016/0228360 on Aug. 11, 2016.
Co-pending PCT Application No. PCT/IB2016/052484 filed May 2, 2016, published as WO 2016/178130 on Nov. 10, 2016.
Co-pending U.S. Appl. No. 15/144,000, filed May 2, 2016, not yet published.
International Preliminary Report on Patentability for International Application No. PCT/IB2015/0055780, issued by US/ISA dated Feb. 9, 2017.
Co-pending U.S. Appl. No. 15/329,070, filed Jan. 25, 2017, not yet published.
Co-pending PCT Application No. PCT/IB2016/052488 filed May 2, 2016, not yet published.
International Search Report and Written Opinion for International Application No. PCT/IB2016/052488, issued by US/ISA dated Aug. 31, 2016.
Co-pending U.S. Appl. No. 15/144,098, filed May 2, 2016, not yet published.
Intuiv: Highlights of prescribing information (201 X Shire US Inc, Revised Feb. 2013).
Medela Breast Milk Bottle Set, Target, published on or before 2010. Available from: www.target.com/p/medela-breast-milk-set-8oz-3ct/-/A-11189915 (Accessed on: Aug. 14, 2017).
Final Office Action for U.S. Appl. No. 15/144,058, issued by USPTO dated Jul. 13, 2017.
Office Action for U.S. Appl. No. 15/144,098, issued by USPTO dated Jul. 13, 2017.
Office Action for U.S. Appl. No. 15/133,773, issued by USPTO dated Aug. 1, 2017.
Office Action for U.S. Appl. No. 15/144,026, issued by USPTO dated Aug. 24, 2017.
Office Action for U.S. Appl. No. 15/148,131, issued by USPTO dated Sep. 29, 2017.
Lopez-Liuchi et al., "Therapy for type 2 diabetes: where do we stand after the UK Prospective Diabetes Sutdy?," European Journal of Endocrinology, 140: 4-6 (1999) Murtaza, "Ethylcellulose Microparticles: A Review," Drug Research, 69(1): 11-22 (2012).
PCT Application No. PCT/IB2015/053207 filed May 1, 2015, published as WO 2015/166472 on Nov. 5, 2015.

(56) References Cited

OTHER PUBLICATIONS

International Search Report and Written Opinion for International Application No. PCT/IB2015/053207, issued by US/ISA dated Aug. 7, 2015.
International Preliminary Report on Patentability for International Application No. PCT/162015/053207, issued by WIPO dated Mar. 16, 2016.
U.S. Appl. No. 15/133,773, filed Apr. 20, 2016, published as U.S. 2016/0228360 on Aug. 11, 2016.
Restriction Requirement for U.S. Appl. No. 15/133,773, issued by USPTO dated Jun. 10, 2016.
Office Action for U.S. Appl. No. 15/133,773, issued by USPTO dated Jul. 27, 2016.
Final Office Action for U.S. Appl. No. 15/133,773, issued by USPTO dated Dec. 16, 2016.
Final Office Action for U.S. Appl. No. 15/133,773, issued by USPTO dated Apr. 13, 2017.
PCT Application No. PCT/IB2016/052484 filed May 2, 2016, published as WO 2016/178130 on Nov. 10, 2016.
International Search Report and Written Opinion for International Application No. PCT/IB2016/052484, issued by US/ISA dated Sep. 8, 2016.
U.S. Appl. No. 15/144,000, filed May 2, 2016, not yet published.
Office Action for U.S. Appl. No. 15/144,000, issued by USPTO dated Jun. 23, 2016.
Final Office Action for U.S. Appl. No. 15/144,000, issued by USPTO dated Nov. 4, 2016.
Office Action for U.S. Appl. No. 15/144,000, issued by USPTO dated Feb. 14, 2017.
Restriction Requirement for U.S. Appl. No. 15/133,826, issued by USPTO dated Jun. 23, 2016.
Final Office Action for U.S. Appl. No. 15/133,826, issued by USPTO dated Dec. 20, 2016.
Office Action for U.S. Appl. No. 15/133,826, issued by USPTO dated Feb. 14, 2017.
Final Office Action for U.S. Appl. No. 15/148,131, issued by USPTO dated Apr. 5, 2017.
Final Office Action for U.S. Appl. No. 15/144,026, issued by USPTO dated Apr. 6, 2017.
International Search Report and Written Opinion for International Application No. PCT/IB2015/055780, issued by US/ISA dated Dec. 7, 2015.
U.S. Appl. No. 15/329,070, filed Jan. 25, 2017, not yet published.
Restriction Requirement for U.S. Appl. No. 15/144,058, issued by USPTO dated Sep. 30, 2016.
Office Action for U.S. Appl. No. 15/144,058, issued by USPTO dated Dec. 16, 2016.
Office Action for U.S. Appl. No. 15/144,058, issued by USPTO dated May 11, 2017.
Office Action for U.S. Appl. No. 15/352,993, issued by USPTO dated Mar. 24, 2017.
PCT Application No. PCT/IB2016/052488 filed May 2, 2016, not yet published.
International Search Report and Written Opinion for International Application No. PCT/182016/052488, issued by US/ISA dated Aug. 31, 2016.
U.S. Appl. No. 15/144,098, filed May 2, 2016, not yet published.
Office Action for U.S. Appl. No. 15/352,993, issued by USPTO dated Aug. 24, 2017.
Final Office Action for U.S. Appl. No. 15/144,000, issued by USPTO dated Aug. 24, 2017.
Continuation U.S. Appl. No. 15/800,682, filed Nov. 1, 2017, not yet published.
Office Action for U.S. Appl. No. 15/329,070, issued by USPTO dated Nov. 21, 2017.
International Preliminary Report on Patentability for International Application No. PCT/IB2016/052485, issued by WIPO dated Nov. 16, 2017.
International Preliminary Report on Patentability for International Application No. PCT/IB2016/052484, issued by WIPO dated Nov. 16, 2017.
International Preliminary Report on Patentability for International Application No. PCT/IB2016/052486, issued by WIPO dated Nov. 16, 2017.
Final Office Action for U.S. Appl. No. 15/133,773, issued by USPTO dated Dec. 11, 2017.
Restriction Requirement for U.S. Appl. No. 15/800,682, issued by USPTO dated Dec. 15, 2017.
Office Action for U.S. Appl. No. 15/144,058, issued by USPTO dated Jan. 16, 2018.
CIP U.S. Appl. No. 15/853,219, filed Dec. 22, 2017, not yet published.
Final Office Action for U.S. Appl. No. 15/352,993, issued by USPTO dated Feb. 8, 2018.
Final Office Action for U.S. Appl. No. 15/144,026, issued by USPTO dated Feb. 7, 2018.

* cited by examiner

EXTENDED RELEASE SUSPENSION COMPOSITIONS

FIELD OF THE INVENTION

The present invention relates to a method for preparing a stable extended release suspension composition comprising multiple coated cores of an active ingredient by using a suspension base, wherein the suspension base ensures substantially similar in-vitro dissolution release profile of the active ingredient upon storage of the suspension compositions for at least seven days.

BACKGROUND OF THE INVENTION

Extended release solid compositions are preferred dosage forms over immediate release solid compositions, especially for active ingredients showing fluctuations in the plasma concentration and for active ingredients having short half-lives. Extended release solid compositions can be in the form of tablets or capsules, wherein the release of the active ingredient is controlled by using a reservoir or a matrix system. However, extended release solid oral compositions suffer from certain drawbacks such as difficulty in swallowing, particularly for certain groups of patients, e.g., pediatrics and geriatrics, resulting in poor patient compliance. Further, high doses of active ingredient lead to large-sized compositions which aggravates this problem. Also, there remains a tendency to divide extended release solid compositions such as tablets into small pieces in order to facilitate administration, which may ultimately lead to inaccurate dosing and/or dose dumping. In view of all this, extended release liquid compositions provide the best alternative over extended release solid compositions. Extended release liquid compositions are easy to administer, thereby leading to enhanced patient compliance. Additionally, extended release liquid compositions provide a unique advantage of having a flexible dosing regimen.

Although extended release liquid compositions are advantageous, there remain some complexities involved in formulating such compositions. The important prerequisite of these compositions is to provide the desired extended release of the active ingredient throughout its shelf life, as irregular release may lead to sub-therapeutic or toxic effects. The key hurdle remains to overcome the leaching of the active ingredient from the coated cores into a suspension base during storage. The objective for a scientist remains to develop a formulation such that the release of the active ingredient into the suspension base during storage is avoided, and only when the suspension enters the gastrointestinal tract the release is allowed.

The prior art discloses various approaches to overcome the leaching problem for the preparation of extended release liquid compositions.

PCT Publication No. WO 2012/063257 and U.S. Publication No. 2008/0118570 disclose extended release suspensions employing ion-exchange resins. Although ion-exchange resin systems provide the desired extended release of the active ingredient without significant leaching during storage, these systems require chemical binding of the active ingredient to the resin, which is complicated and not suitable for many active ingredients.

PCT Publication No. WO 2011/107855 discloses a ready to use sustained release oral suspension comprising inert pellets surrounded by a seal coating, an active ingredient layer surrounding the seal coated inert pellets, and a coating layer comprising a rate-controlling polymer surrounding the active ingredient layer. Said sustained release pellets are further coated with a protective coating layer which prevents the leaching of the active ingredient.

PCT Publication No. WO 2008/122993 discloses a suspension of an active ingredient containing microparticles with at least one coat of a pH-independent polymer. Further, there is an additional coat of pH-dependent polymer which provides stability to the formulation by avoiding leaching of active ingredient in the liquid phase after reconstitution during storage.

In the formulations disclosed in these prior art, the leaching of the active ingredients from the coated units into the media during storage is primarily prevented by the use of a multiple coating systems. However, the process of applying multiple coating systems remains time-consuming, complicated, and difficult to be functionally reproducible.

U.S. Pat. No. 7,906,145 discloses a sustained release suspension comprising microcapsules suspended in an aqueous liquid phase saturated with an active ingredient, wherein each microcapsule comprises a core of the active ingredient and a coating layer applied to the core which controls the modified release of the active ingredient in gastrointestinal fluids. Said coating layer comprises a film-forming polymer, a nitrogen-containing polymer, a plasticizer, and a surfactant/lubricant. The coating layer is designed in a way such that the release profile is not perturbed in the liquid phase and the active ingredient contained in the microcapsules is prevented from escaping into the liquid phase throughout the storage of the suspension. However, this system also requires mandatory use of an aqueous phase saturated with the active ingredient which may not be suitable for active ingredients having low aqueous solubility and/or low dose. Further, this system is limited to class of active ingredients which require an immediate dose or an initial spike in the release profile and therefore is not suitable for active ingredients which do not require any immediate dose of the active ingredient. Also, the aqueous phase saturated with the active ingredient remains physically unstable as a small variation in temperature, pH, and/or ionic concentration may lead to salting out or precipitation of the active ingredient.

In view of all these, there remains a need in the art to formulate extended release suspension compositions of the active ingredients which are based on a simplified and robust technology and which provide significant advancement over the existing prior art. The extended release suspension compositions of the present invention are suitable for variety of active ingredients including active ingredients having low aqueous solubility or active ingredients which do not require any immediate dose of the active ingredient. The extended release suspension compositions of the present invention remain physically stable to any variation in temperature, pH, and/or ionic concentration. Furthermore, the extended release suspension compositions of the present invention provide the desired extended release throughout the shelf life of the compositions.

The present invention provides extended release suspension compositions based on a simplified technology, prepared by a process which is relatively simple, easy to commercially manufacture, and functionally reproducible. The present invention uses a unique suspension base which prevents the leaching of the active ingredient from the coated cores during storage. The suspension base thus ensures substantially similar in-vitro dissolution release profile of the active ingredient upon storage throughout the shelf life of the compositions. This consistent in-vitro release then ensures a steady plasma concentration with no fluctuations throughout the shelf life of the compositions.

Additionally, the extended release suspension compositions of the present invention are able to incorporate two or more active ingredients with different release profiles or two or more incompatible active ingredients in a single composition.

SUMMARY OF THE INVENTION

The present invention relates to a method for preparing a stable extended release suspension composition comprising multiple coated cores of an active ingredient by using a suspension base, wherein the suspension base ensures substantially similar in-vitro dissolution release profile of the active ingredient upon storage of the suspension composition for at least seven days.

The extended release suspension composition of the present invention is easy to administer, thereby leading to enhanced patient compliance. Further, said extended release suspension composition provides better dose flexibility depending on the age and body weight of the patient. Also, said extended release suspension composition is stable, easy to commercially manufacture, and provide reproducible bioavailability. Additionally, said extended release suspension composition provides a pleasant mouth feel and taste masking for bitter drugs, thereby further enhancing patient compliance. The present invention provides such composition and improves patient compliance by reducing dosing frequency for pediatric as well as geriatric patients.

DETAILED DESCRIPTION OF THE INVENTION

Figure 1:
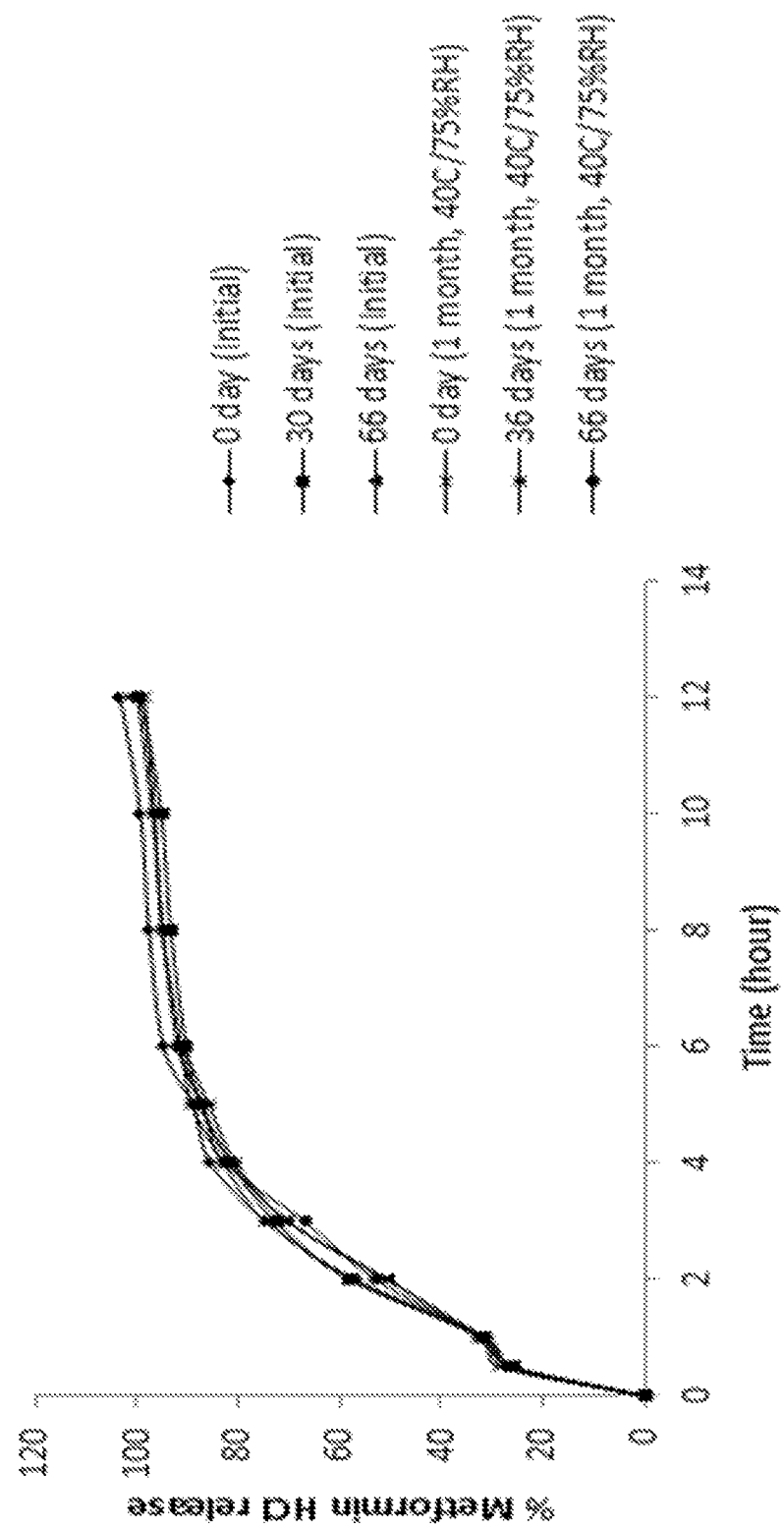
FIG. 1 shows the in-vitro dissolution release on day 0, day 30, and day 66 of the extended release suspension composition prepared according to Example 4 upon storage at room temperature. This figure also shows the in-vitro dissolution release on day 0, day 36, and day 66 of the extended release suspension composition (at room temperature) formed after reconstituting the powder stored for one month at accelerated conditions.

A first aspect of the present invention provides a method for preparing a stable extended release suspension composition comprising multiple coated cores of an active ingredient by using a suspension base, wherein the suspension base ensures substantially similar in-vitro dissolution release profile of the active ingredient upon storage of the suspension composition for at least seven days.

According to one embodiment of the above aspect, the suspension base is characterized by having the features of:
(i) a viscosity in a range of about 500 cps to about 15,000 cps; and
(ii) an osmolality of at least about 1 osmol/kg of the suspension base.

According to another embodiment of the above aspect, the suspension base comprises:
(i) a suspending agent;
(ii) an osmogent; and
(iii) an aqueous vehicle.

According to another embodiment of the above aspect, the suspension base does not include a saturated solution of the active ingredient.

According to another embodiment of the above aspect, the suspension base generates a hypertonic condition such that there is no substantial change in the in-vitro dissolution release profile of the active ingredient upon storage of the extended release suspension composition for at least seven days.

According to another embodiment of the above aspect, the stable extended release suspension composition is characterized by having an osmolality ratio of at least about 1.

According to another embodiment of the above aspect, the coated core comprises a core of the active ingredient and a coating layer over said core comprising one or more release-controlling agents.

According to another embodiment of the above aspect, the core of the active ingredient is in the form of a bead, a pellet, a granule, a spheroid, or the like.

According to another embodiment of the above aspect, the active ingredient is layered onto an inert particle to form the core.

According to another embodiment of the above aspect, the inert particle is selected from the group comprising a non-pareil seed, a microcrystalline cellulose sphere, a dibasic calcium phosphate bead, a mannitol bead, a silica bead, a tartaric acid pellet, a sugar bead, or a wax based pellet.

According to another embodiment of the above aspect, the average diameter of the coated cores ranges from about 10 µm to about 2000 µm. In a preferred embodiment, the average diameter of the coated cores ranges from about 50 µm to about 1000 µm. In a more preferred embodiment, the average diameter of the coated cores ranges from about 150 µm to about 500 µm.

According to another embodiment of the above aspect, the stable extended release suspension composition is a taste-masked composition.

According to another embodiment of the above aspect, the stable extended release suspension composition is in the form of a suspension or a reconstituted powder for suspension.

According to another embodiment of the above aspect, the release-controlling agent is selected from the group comprising a pH-dependent release-controlling agent, a pH-independent release-controlling agent, or mixtures thereof.

A second aspect of the present invention provides a process for the preparation of a stable extended release suspension composition, wherein the process comprises the steps of:
(i) preparing cores comprising an active ingredient and one or more pharmaceutically acceptable excipients;
(ii) dissolving/dispersing a release-controlling agent and one or more pharmaceutically acceptable coating additives in a suitable solvent;
(iii) applying the coating composition of step (ii) over the cores of step (i);

(iv) dissolving/dispersing one or more suspending agents, one or more osmogents, and optionally one or more pharmaceutically acceptable excipients into an aqueous vehicle to form a suspension base; and
(v) dispersing the coated cores of step (iii) in the suspension base of step (iv) to obtain the stable extended release suspension composition.

A third aspect of the present invention provides a process for the preparation of a stable extended release suspension composition, wherein the process comprises the steps of:
(A) preparing a powder for suspension comprising the steps of:
  (i) preparing cores comprising an active ingredient and one or more pharmaceutically acceptable excipients;
  (ii) dissolving/dispersing a release-controlling agent and one or more pharmaceutically acceptable coating additives in a suitable solvent;
  (iii) applying the coating composition of step (ii) over the cores of step (i);
  (iv) mixing one or more pharmaceutically acceptable excipients with the coated cores of step (iii) to obtain the powder for suspension;
(B) preparing a suspension base by dissolving/dispersing one or more suspending agents, one or more osmogents, and optionally one or more pharmaceutically acceptable excipients into an aqueous vehicle; and
(C) reconstituting the powder for suspension of step (A) with a suspension base of step (B) to obtain the extended release suspension composition.

A fourth aspect of the present invention provides a process for the preparation of a stable extended release suspension composition, wherein the process comprises the steps of:
(A) preparing a powder for suspension comprising the steps of:
  (i) preparing cores comprising an active ingredient and one or more pharmaceutically acceptable excipients;
  (ii) dissolving/dispersing a release-controlling agent and one or more pharmaceutically acceptable coating additives in a suitable solvent;
  (iii) applying the coating composition of step (ii) over the cores of step (i);
  (iv) mixing one or more suspending agents, one or more osmogents and optionally one or more pharmaceutically acceptable excipients with the coated cores of step (iii) to obtain the powder for suspension; and
(B) reconstituting the powder for suspension of step (A) with an aqueous vehicle to obtain the extended release suspension composition.

The term "extended release," as used herein, refers to the release profile of the active ingredient over an extended period of time, e.g., over a period of 4, 6, 8, 12, 24 hours, or more.

The term "osmolality ratio," as used herein, means the ratio of the osmolality of the external phase to the osmolality of the internal phase. The external phase herein, means the suspension base without multiple coated cores of the active ingredient. The internal phase herein means the coated cores of the active ingredient. As the direct measurement of the osmolality of the internal phase i.e., coated cores is difficult, the osmolality of the internal phase herein, is represented as the osmolality of a solution which prevents significant leaching of the active ingredient from the coated cores into the solution. The leaching of the active ingredient from the coated cores is determined by the difference in the osmolalities across the coating layer and the absence of any significant leaching from the coated cores directs that the osmolality of the solution has become equal to the osmolality of the coated cores. The osmolality ratio of the extended release suspension compositions of present invention is at least about 1.

The term "hypertonic condition," as used herein, means the suspension base has higher solute concentration which helps to generate high osmotic pressure such that there is no leaching of the active ingredient from the coated cores into the suspension base. In the present invention, the solutes are osmogents i.e., pharmaceutically acceptable inert water-soluble compounds that contribute towards generating hypertonic conditions in the suspension base.

The term "osmolality," as used herein, is expressed as number of moles of any water-soluble compound per kg of a liquid phase. The liquid phase can be a suspension base or a solution. In the present invention, the osmolality may be measured according to known methods, such as using a vapor pressure osmometer, a colloid osmometer, or a freezing point depression osmometer such as Osmomat® 030-D or Osmomat® 3000, in particular by a freezing point depression osmometer. The suspension base of the present invention has an osmolality of at least about 1 osmol/kg of the suspension base. In particular, the suspension base of the present invention has an osmolality of at least about 2 osmol/kg of the suspension base. The suspension base of the present invention has an osmolality ranging from about 1 osmol/kg to about 20 osmol/kg of the suspension base.

The osmolality of the suspension base of the extended release suspension compositions of the present invention remains equivalent upon storage for at least seven days. Particularly, the osmolality of the suspension base measured after one month remains equivalent to the osmolality of the suspension base measured as soon as practicable after preparation of the extended release suspension compositions. More particularly, the osmolality of the suspension base measured after three months or six months remains equivalent to the osmolality of the suspension base measured as soon as practicable after preparation of the extended release suspension compositions. The equivalent osmolality of the suspension base ensures that there is no leaching of the active ingredient from the coated cores into the suspension base.

The viscosity of the suspension base of the present invention ranges from about 500 cps to about 15,000 cps. Preferably, the viscosity of the suspension base ranges from about 1,000 cps to about 10,000 cps. More preferably, the viscosity of the suspension base ranges from about 2,000 cps to about 7,000 cps. The viscosity of the suspension base of the present invention is measured by using a Brookfield Viscometer having a #2 spindle rotating at 5 rpm at 25° C.

The term "stable," as used herein, refers to chemical stability, wherein not more than 5% w/w of total related substances are formed on storage at 40° C. and 75% relative humidity (R.H.) or at 25° C. and 60% R.H. for a period of at least three months to the extent necessary for the sale and use of the composition.

The term "inert particle," as used herein, refers to a particle made from a sugar sphere also known as a nonpareil seed, a microcrystalline cellulose sphere, a dibasic calcium phosphate bead, a mannitol bead, a silica bead, a tartaric acid pellet, a wax based pellet, and the like.

The term "about," as used herein, refers to any value which lies within the range defined by a variation of up to ±10% of the value.

The term "equivalent" as used herein, refers to any value which lies within the range defined by a variation of up to ±30% of the value.

The term "significant leaching," as used herein means more than 20% of the active ingredient is leached out from the coated cores into the solution.

The in-vitro dissolution release profile of the extended release suspension composition of the present invention upon storage for at least seven days remains substantially similar to the initial in-vitro dissolution release profile obtained as soon as practicable after preparation of the extended release suspension composition. Particularly, the in-vitro dissolution release profile of the extended release suspension composition of the present invention upon storage for at least one month remains substantially similar to initial in-vitro dissolution release profile obtained as soon as practicable after preparation of the extended release suspension composition. More particularly, the in-vitro dissolution release profile of the extended release suspension composition of the present invention upon storage for at least three months remains substantially similar to initial in-vitro dissolution release profile obtained as soon as practicable after preparation of the extended release suspension compositions. More particularly, the in-vitro dissolution release profile of the extended release suspension composition of the present invention upon storage for at least six months remains substantially similar to initial in-vitro dissolution release profile obtained as soon as practicable after preparation of the extended release suspension composition. In the present invention, wide ranges of dissolution methodologies can be utilized for different active ingredients. These methodologies can be adopted to vary in hydrodynamic mechanism to simulate in-vivo conditions by using different dissolution apparatuses, volume of media, pH of media ranging from 1.0 to 7.5, any standard USP buffers with standard molarity, addition of surfactants, and or enzymes.

The extended release suspension composition of the present invention provides the consistent in-vivo release which ensures steady and predictable active ingredient release with minimal inter and intra subject variation throughout the shelf life of the composition.

The term "substantial," as used herein refers to any value which lies within the range as defined by a variation of up to ±15 from the average value.

The term "suspension base," as used herein, refers to a medium which is used to suspend the coated cores of the active ingredient. The suspension base of the present invention is characterized by having a viscosity in a range of about 500 cps to about 15,000 cps; and an osmolality of at least about 1 osmol/kg of the suspension base.

The suspension base generates a hypertonic condition such that there is no substantial change in the in-vitro dissolution release profile of the active ingredient upon storage of the suspension composition for at least seven days. Alternatively, the suspension base may have a pH such that there is no substantial change in the in-vitro dissolution release profile of the active ingredient upon storage of the suspension composition for at least seven days. In this case, the active ingredient may have a pH-dependent solubility and the pH of the suspension base is adjusted to a predetermined pH at which the active ingredient remains substantially insoluble.

The extended release suspension composition of the present invention may be in the form of a suspension or a reconstituted powder for suspension.

The suspension base of the present invention comprises one or more suspending agents, one or more osmogents, and an aqueous vehicle. It may further comprise one or more pharmaceutically acceptable excipients. The powder for suspension having coated cores of active ingredient of the present invention may be reconstituted with the suspension base having suspending agents, osmogents, pharmaceutically acceptable excipients, and an aqueous vehicle. Alternatively, suspending agents, osmogents, or other pharmaceutically acceptable excipients may be premixed with the coated cores which may be reconstituted with an aqueous vehicle. In case of powder for suspension, the suspension base may be pre-formed or formed at the time of reconstitution.

The aqueous vehicle may comprise of purified water or a mixture of purified water with one or more suitable organic solvents.

The average diameter of the coated cores of the present invention ranges from about 10 μm to about 2000 μm, particularly from about 50 μm to about 1000 μm, and more particularly from about 150 μm to about 500 μm. The finer sizes of the coated cores help in avoiding grittiness in the mouth and are therefore more acceptable. The cores of the present invention may comprise one or more pharmaceutically acceptable excipients such as a binder, a release-controlling agent, an osmogent, a stabilizer, a solubilizer, or a pH modifying agent. The stabilizer may include but not limited to a pH modifying agent, a chelating agent, or an anti-oxidant. The solubilizer may include but not limited to a solubility enhancing agent, a pH modifying agent, an adsorbent, or a complexing agent.

The active ingredient of the present invention includes any active ingredient belonging to a therapeutic category, including but not limited to antidiabetic, antibiotic, antimicrobial, analgesic, antiallergic, antianxiety, antiasthmatic, anticancer, antidepressant, antiemetic, antiinflammatory, anti-Parkinson's, antiepileptic, antitussive, antiviral, immunosuppressant, diuretic, antimigraine, antihypertensive, hypolipidemics, anti-arrhythmics, vasodilators, anti-anginals, sympathomimetic, cholinomemetic, adrenergic, antimuscarinic, neuroleptics, antispasmodic, skeletal muscle relaxants, expectorants, and drugs for treating attention deficit hyperactive disorder. The active ingredient of the present invention can be present in the form of a free base or in the form of pharmaceutically acceptable salts. Specific examples of active ingredients include but are not limited to the group comprising metformin, acarbose, miglitol, voglibose, repaglinide, nateglinide, glibenclamide, glimepride, glipizide, gliclazide, chloropropamide, tolbutamide, phenformin, aloglitin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, verapamil, albuterol, salmeterol, acebutolol, sotalol, penicillamine, norfloxacin, ciprofloxacin, ofloxacin, levofloxacin, moxifloxacin, trovafloxacin, gatifloxacin, cefixime, cefdinir, cefprozil, cefadroxil, cefuroxime, cefpodoxime, tetracycline, demeclocycline hydrochloride, amoxicillin, clavulanate potassium, azithromycin, losartan, irbesartan, eprosartan, valsartan, diltiazem, isosorbide mononitrate, ranolazine, propafenone, hydroxyurea, hydrocodone, delavirdine, pentosan polysulfate, abacavir, amantadine, acyclovir, ganciclovir, valacyclovir, valganciclovir, saquinavir, indinavir, nelfinavir, lamivudine, didanosine, zidovudine, nabumetone, celecoxib, mefenamic acid, naproxen, propoxyphene, cimetidine, ranitidine, albendazole, mebendazole, thiobendazole, pyrazinamide, praziquantel, chlorpromazine, sumatriptan, bupropion, aminobenzoate, pyridostigmine bromide, potassium chloride, niacin, tocainide, quetiapine, fexofenadine, sertraline, chlorpheniramine, rifampin, methenamine, nefazodone, modafinil, metaxalone, morphine, sevelamer, lithium carbonate, flecainide acetate, simethicone, methyldopa, chlorthiazide, metyrosine, procainamide, entacapone, metoprolol, propanolol hydrochloride, chlorzoxazone, tolmetin, tramadol, bepridil, phenytoin, gabapentin, fluconazole, terbinafine, atorvastatin, doxepine, rifabutin, mesalamine, etidronate, nitrofurantoin, choline magnesium trisalicylate, theophylline, nizatidine, methocarbamol, mycophenolate mofetil, tolcapone, ticlopidine, capecitabine, orlistat, colsevelam, meperidine, hydroxychloroquine, guaifenesin, guanfacine, amiodarone, quinidine, atomoxetine, felbamate, pseudoephedrine, carisoprodol, venlafaxine, etodolac, chondrotin, lansoprazole, pantoprazole, esomeprazole, dexlansoprazole, dexmethylphenidate, methylphenidate, sodium oxybate, valproic acid or its salts, divalproex, topiramate, carbamazepine, oxcarbazepine, and isotretinoin. The dose of any active ingredient depends upon the individual active ingredient used in the extended release suspension compositions of the present invention. Further, the extended release suspension compositions of the present invention permit ready dose titration, i.e., adjusting the dose of the active ingredient based on recommended dose range and frequency until the desired therapeutic effect is achieved. In particular, the active ingredients used in the present invention are active ingredients with a high dose.

The suspension base may additionally include an immediate release component of the active ingredient. However, the suspension base of the present invention does not include any saturated solution of the active ingredient. The suspension base may include an immediate release component of the active ingredient, wherein the active ingredient is present in an amount that does not exceed the amount required to form the saturated solution either initially or during storage. The active ingredient may be present in the form of a powder, a pellet, a bead, a spheroid, or a granule, or in the form of immediate release coating over the extended release coated cores. Alternatively, the amount of active ingredient may exceed the amount required to form the saturated solution. However, the saturated solution of active ingredient is not formed, as the release of active ingredient into the suspension base is prevented during storage. This is achieved by using a coating layer over the cores of the active ingredient, wherein the coating layer comprises a polymer that remain insoluble in the suspension base during storage and which releases the active ingredient in the immediate release form once ingested. Alternatively, this can also be done by using a complexation approach such as an ion-exchange resin complex, wherein the complex prevents any release of the active ingredient into the suspension base during storage, and releases the active ingredient only when exposed to the physiological conditions upon ingestion. The polymer can be a water-soluble polymer in which the release of active ingredient is prevented by using a high molar concentration of the solutes in the suspension base, wherein the solutes have a higher affinity towards water in comparison to the polymer. Further, the polymer can be having a pH-dependent solubility in which the release of active ingredient is prevented by using a pre-adjusted pH of the suspension base such that the polymer does not get dissolved in the suspension base but get dissolved when exposed to the physiological conditions. For instance, acrylic polymers available under the trade mark Eudragit® E and Eudragit® EPO are soluble at an acidic pH. The pH of the suspension base can be pre-adjusted to a basic pH such that the coating does not get dissolved during storage but get dissolved in the stomach when ingested.

The immediate release component may help in providing an immediate therapeutic effect which could be subsequently followed by an extended therapeutic effect over a longer duration of time once ingested. Depending upon the type of polymer and percentage weight gain of the coating, the lag between the two phases can be adjusted to get the desired release profile.

Further, the extended release suspension composition of the present invention may comprise two or more similar or different active ingredients with different type of release profiles.

The extended release suspension composition of the present invention may also comprise two or more incompatible active ingredients present in a single composition. One of the active ingredients would be present in the form of coated cores providing the extended release and another incompatible active ingredient may be present in the form of a powder, a pellet, a bead, a spheroid, or a granule providing the immediate release or the extended release.

The extended release suspension compositions of the present invention are homogeneous which means the compositions provide the content uniformity and deliver the desired dose of the active ingredient in every use without any risk of overdosing or underdosing.

The release-controlling agents used to form the extended release coating are selected from a group comprising a pH-dependent release-controlling agent, a pH-independent release-controlling agent, or mixtures thereof. For an extended release coating comprising a pH-dependent release-controlling agent, the pH of the suspension base is pre-adjusted such that the coating remains insoluble in the suspension base during the storage. The extended release coating comprising a pH-dependent release-controlling agent may alternatively be coated with a coating layer comprising a polymer such that said coating layer remain insoluble in the suspension base during storage. The core may comprise release-controlling agents in the form of a matrix with the active ingredient, which can be coated with a coating layer that remain insoluble in the suspension base during storage.

Suitable examples of pH-dependent release-controlling agent are selected from the group comprising acrylic copolymers such as methacrylic acid and methyl methacrylate copolymers, e.g., Eudragit® L 100 and Eudragit® S 100, methacrylic acid and ethyl acrylate copolymers, e.g., Eudragit® L 100-55 and Eudragit® L 30 D-55, dimethylaminoethyl methacrylate and butyl methacrylate and methyl methacrylate copolymers e.g., Eudragit® E 100, Eudragit® E PO, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

Suitable examples of pH-independent release-controlling agent are selected from the group comprising cellulosic polymers such as ethyl cellulose, methyl cellulose, hydroxyethyl cellulose, hydroxypropyl cellulose, hydroxyethylmethyl cellulose, hydroxypropylmethyl cellulose, and carboxy methylcellulose; acrylic copolymers such as methacrylic acid copolymers, e.g., Eudragit® RS, Eudragit® RL, Eudragit® NE 30 D; cellulose acetate; polyethylene derivatives e.g., polyethylene glycol and polyethylene oxide; polyvinyl alcohol; polyvinyl acetate; gums e.g., guar gum, locust bean gum, tragacanth, carrageenan, alginic acid, gum acacia, gum arabic, gellan gum, and xanthan gum; triglycerides; waxes, e.g., Compritol®, Lubritab®, and Gelucires®; lipids; fatty acids or their salts/derivatives; a mixture of polyvinyl acetate and polyvinyl pyrrolidone, e.g., Kollidon® SR; and mixtures thereof.

The term "osmogent," as used herein, refers to all pharmaceutically acceptable inert water-soluble compounds that can imbibe water and/or aqueous biological fluids. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide; xanthan gum; hydroxypropylmethyl cellulose; and mixtures thereof. Particularly, the osmogents used in the present invention are xylitol, mannitol, glucose, lactose, sucrose, and sodium chloride.

Suitable suspending agents are selected from the group comprising cellulose derivatives such as co-processed spray dried forms of microcrystalline cellulose and carboxymethyl cellulose sodium, hydroxypropyl cellulose, hydroxyethyl cellulose, hydroxypropylmethyl cellulose, methylcellulose, carboxymethyl cellulose and its salts/derivatives, and microcrystalline cellulose; carbomers; gums such as locust bean gum, xanthan gum, tragacanth gum, arabinogalactan gum, agar gum, gellan gum, guar gum, apricot gum, karaya gum, sterculia gum, acacia gum, gum arabic, and carrageenan; pectin; dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; and mixtures thereof. Co-processed spray dried forms of microcrystalline cellulose and carboxymethyl cellulose sodium have been marketed under the trade names Avicel® RC-501, Avicel® RC-581, Avicel® RC-591, and Avicel® CL-611. The suspending agent is present in an amount of not more than about 20% w/w, based on the total weight of the suspension base.

The term "pharmaceutically acceptable excipients," as used herein, refers to excipients that are routinely used in pharmaceutical compositions. The pharmaceutically acceptable excipients may comprise glidants, sweeteners, anti-caking agents, wetting agents, preservatives, buffering agents, flavoring agents, anti-oxidants, chelating agents, solubility enhancing agents, pH modifying agents, adsorbents, complexing agents, and combinations thereof.

Suitable glidants are selected from the group comprising silica, calcium silicate, magnesium silicate, colloidal silicon dioxide, cornstarch, talc, stearic acid, magnesium stearate, calcium stearate, sodium stearyl fumarate, hydrogenated vegetable oil, and mixtures thereof.

Suitable sweeteners are selected from the group comprising saccharine or its salts such as sodium, potassium, or calcium, cyclamate or its salt, aspartame, alitame, acesulfame or its salt, stevioside, glycyrrhizin or its derivatives, sucralose, and mixtures thereof.

Suitable anti-caking agents are selected from the group comprising colloidal silicon dioxide, tribasic calcium phosphate, powdered cellulose, magnesium trisilicate, starch, and mixtures thereof.

Suitable wetting agents are selected from the group comprising anionic, cationic, nonionic, or zwitterionic surfactants, or combinations thereof. Suitable examples of wetting agents are sodium lauryl sulphate; cetrimide; polyethylene glycols; polyoxyethylene-polyoxypropylene block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid esters such as polyoxyethylene sorbitan monooleate; polyethylene glycol fatty acid esters such as polyoxyethylene monostearate; polyoxyethylene alkyl ethers such as polyoxyethylene lauryl ether; polyoxyethylene castor oil; and mixtures thereof.

Suitable preservatives are selected from the group comprising parabens such as methyl paraben and propyl paraben; sodium benzoate; and mixtures thereof.

Suitable buffering agents are selected from the group comprising citric acid, sodium citrate, sodium phosphate, potassium citrate, acetate buffer, and mixtures thereof.

Suitable flavoring agents are selected from the group consisting of peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloe vera balsam, spearmint, eucalyptus, and combinations thereof.

Suitable anti-oxidants are selected from the group comprising butylated hydroxytoluene (BHT), butylated hydroxyanisole (BHA), sodium metabisulfite, ascorbic acid, propyl gallate, thiourea, tocopherols, beta-carotene, and mixtures thereof.

Suitable chelating agents are selected from the group comprising ethylenediamine tetraacetic acid or derivatives/salts thereof, e.g., disodium edetate; dihydroxyethyl glycine; glucamine; acids, e.g., citric acid, tartaric acid, gluconic acid, and phosphoric acid; and mixtures thereof.

Suitable binders are selected from the group comprising polyvinyl pyrrolidone, starch, pregelatinized starch, hydroxypropylmethyl cellulose, hydroxyethyl cellulose, methyl cellulose, sodium carboxymethyl cellulose, gums, acrylate polymers, and mixtures thereof.

Suitable pH modifying agents are selected from the group comprising fumaric acid, citric acid, tartaric acid, oxalic acid, malic acid, maleic acid, succinic acid, ascorbic acid, pyruvic acid, malonic acid, glutaric acid, adipic acid, gluconic acid, lactic acid, aspartic acid, sulfamic acid, sodium hydrogen carbonate, potassium hydrogen carbonate, sodium carbonate, potassium carbonate, magnesium carbonate, and calcium carbonate, and mixtures thereof.

Suitable solubility enhancing agents are selected from the group comprising surfactants such as nonionic e.g., polyoxyethylene sorbitan fatty acid esters, sorbitan esters, polyoxyethylene ethers, anionic e.g., sodium lauryl sulfate, sodium laurate, dialkyl sodium sulfosuccinates, particularly bis-(2-ethylhexyl) sodium sulfosuccinate, sodium stearate, potassium stearate, and sodium oleate, cationic e.g., benzalkonium chloride and bis-2-hydroxyethyl oleyl amine, and zwitterionic surfactants; fatty alcohols such as lauryl, cetyl, and stearyl alcohols; glyceryl esters such as the naturally occurring mono-, di-, and tri-glycerides; fatty acid esters of fatty alcohols and other alcohols such as propylene glycol, polyethylene glycol; sucrose; polymers e.g., poloxamers such as those available under the trade name Pluronic®, polyvinylpyrrolidones, glycerides e.g., triacetin, glyceryl monocaprylate, glyceryl monooleate, glyceryl monostearate; diethylene glycol monoethyl ether; and combinations thereof.

Suitable adsorbents are selected from the group comprising silica (silicon dioxide); silicates; magnesium trisilicate; magnesium aluminium silicate; calcium silicate; magnesium hydroxide; talcum; crospovidone, kaolin; cyclodextrin and its derivatives; propylene glycol alginate; celluloses e.g., cellulose powder, microcrystalline cellulose, ethyl cellulose, methyl cellulose, calcium carboxymethyl cellulose, sodium carboxymethyl cellulose, hydroxyethyl cellulose, hydroxymethyl cellulose, hydroxypropyl cellulose, hydroxypropylmethyl cellulose, cross-linked sodium carboxymethyl cellulose; cross-linked polymethyl methacrylate; poloxamer; povidone and its derivatives; sodium starch glycolate; and combinations thereof.

Suitable complexing agents are selected from the group comprising crospovidone, povidone, cyclodextrin and its derivatives, and combinations thereof.

The ion-exchange resins such as cation- and anion-exchange matrices are well-known in the art. Few exemplary resin particles that can be used according to the invention include, but are not limited to, Dowex® resins and others made by Dow Chemical; Amberlite®, Amberlyst® and other resins made by Rohm and Haas; Indion® resins made by Ion Exchange, Ltd. (India), Diaion® resins by Mitsubishi; Type AGO and other resins by BioRad; Sephadex® and Sepharose® made by Amersham; resins by Lewatit, sold by Fluka; Toyopearl® resins by Toyo Soda; IONAC® and Whatman® resins sold by VWR; and BakerBond® resins sold by J T Baker; cholestyramine; resins having polymer backbones comprising styrene-divinyl benzene copolymers and having pendant ammonium or tetraalkyl ammonium functional groups, available from Rohm and Haas, Philadelphia, and sold under the tradename DUOLITE™ AP143; or any mixtures thereof.

The cores of the present invention comprising the active ingredient can be prepared by any method known in the art, e.g., extrusion-spheronoization, wet granulation, dry granulation, hot-melt extrusion granulation, spray drying, and spray congealing. Alternatively, the active ingredient can be layered onto an inert particle to form the core.

Further, the active ingredient particles can be directly coated with a release-controlling agent to form the microparticles or microcapsules. The microparticles or microcapsules can be prepared by a process of homogenization, solvent evaporation, coacervation phase separation, spray drying, spray congealing, polymer precipitation, or supercritical fluid extraction.

The extended release suspension compositions of the present invention may further comprise one or more seal coating layers which may be applied before and/or after the functional coating layer. The seal coating layer may comprise of one or more film-forming polymers and coating additives.

Examples of film-forming polymers include ethylcellulose, hydroxypropyl methylcellulose, hydroxypropylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; methacrylic acid polymers such as Eudragit®. Alternatively, commercially available coating compositions comprising film-forming polymers marketed under various trade names, such as Opadry® may also be used.

The coating additives used in the present invention are selected from the group comprising plasticizers, opacifiers, anti-tacking agents, surfactants, coloring agents, and combinations thereof.

Suitable plasticizers are selected from the group comprising triethyl citrate, dibutylsebacate, triacetin, acetylated triacetin, tributyl citrate, glyceryl tributyrate, diacetylated monoglyceride, rapeseed oil, olive oil, sesame oil, acetyl tributyl citrate, acetyl triethyl citrate, glycerin, sorbitol, diethyl oxalate, diethyl phthalate, diethyl malate, diethyl fumarate, dibutyl succinate, diethyl malonate, dioctyl phthalate, and combinations thereof.

Suitable opacifiers are selected from the group comprising titanium dioxide, manganese dioxide, iron oxide, silicon dioxide, and combinations thereof.

Suitable anti-tacking agents are selected from the group comprising silica, calcium silicate, magnesium silicate, colloidal silicon dioxide, cornstarch, talc, stearic acid, magnesium stearate, calcium stearate, sodium stearyl fumarate, hydrogenated vegetable oil, glyceryl monostearate, and mixtures thereof.

Suitable surfactants are selected from the group comprising anionic, cationic, nonionic, or zwitterionic surfactants, or combinations thereof. Examples of surfactants include sodium lauryl sulphate; cetrimide; polyethylene glycols; polyoxyethylene-polyoxypropylene block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid esters such as polyoxyethylene sorbitan monooleate; polyethylene glycol fatty acid esters such as polyoxyethylene monostearate; polyoxyethylene alkyl ethers such as polyoxyethylene lauryl ether; polyoxyethylene castor oil; and mixtures thereof.

Suitable coloring agents are selected from the group consisting of FD&C (Federal Food, Drug and Cosmetic Act) approved coloring agents; natural coloring agents; natural juice concentrates; pigments such as iron oxide, titanium dioxide, and zinc oxide; and combinations thereof.

Coating may be performed by applying the coating composition as a solution/suspension/blend using any conventional coating technique known in the art such as spray coating in a conventional coating pan, fluidized bed processor, dip coating, or compression coating. The percentage of the coating build-up shall be varied depending on the required extended release.

Suitable solvents used for granulation or for forming a solution or dispersion for coating are selected from the group consisting of water, ethanol, methylene chloride, isopropyl alcohol, acetone, methanol, and combinations thereof.

The extended release suspension compositions of the present invention may be packaged in a suitable package such as a bottle. The powder for suspension may be packaged in a suitable package such as a bottle or a sachet. Further, the sachet can be filled as a unit dose or a multidose sachet. The present invention further includes a co-package or a kit comprising two components, wherein one package or one component comprises a powder for suspension and another package or another component comprises a suspension base or an aqueous vehicle. Alternatively, a dual chamber pack with two chambers can be used. In this case, one chamber comprises a powder for suspension and another chamber comprises a suspension base or an aqueous vehicle.

The invention may be further illustrated by the following examples, which are for illustrative purposes only and should not be construed as limiting the scope of the invention in any way.

EXAMPLES

Example 1

| Ingredients | Quantity (mg/mL) |
|---|---|
| Core | |
| Metformin hydrochloride | 100.00 |
| Microcrystalline cellulose spheres | 90.00 |
| Hydroxypropylmethyl cellulose | 5.00 |
| Purified water | q.s. |
| Extended Release Coating | |
| Ethyl cellulose | 61.42 |
| Dibutyl sebacate | 6.82 |
| Acetone | q.s. |
| Purified water | q.s. |
| Total Weight of Extended Release Beads | 263.24 mg |
| Xylitol | 450.00 |
| Xanthan gum | 1.500 |
| Microcrystalline cellulose - sodium carboxymethyl cellulose (Avicel ® CL 611) | 20.00 |
| Strawberry flavor | 1.50 |
| Vehicle | |
| Purified water | q.s. to 1 mL |

Procedure:

1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Xylitol, xanthan gum, microcrystalline cellulose-sodium carboxymethyl cellulose, and strawberry flavor were mixed with the coated beads of step 4.
6. The mixture of step 5 was dispersed in required amount of purified water to obtain the extended release suspension composition.

In-Vitro Studies

In-vitro release of metformin from the extended release suspension composition prepared as per Example 1 was determined by the dissolution for metformin using USP type II apparatus at 100 rpm, in 1000 mL of phosphate buffer with pH 6.8 at 37° C. The results of the release studies are represented in Table 1.

TABLE 1

Percentage (%) of the In-Vitro Metformin Release in USP Type II Apparatus (Media: Phosphate Buffer, pH 6.8, 1000 mL, and 100 rpm)

| Time (hours) | Number of Days | | |
|---|---|---|---|
| | 0 | 15 | 30 |
| | Percentage of Metformin Release | | |
| 2 | 9 | 9 | 10 |
| 3 | 34 | 35 | 37 |
| 4 | 56 | 57 | 57 |
| 5 | 69 | 69 | 68 |
| 6 | 76 | 76 | 75 |
| 8 | 85 | 85 | 84 |
| 10 | 90 | 92 | 89 |
| 12 | 93 | 94 | 92 |

From the above data, it is clear that the extended release suspension composition prepared according to Example 1 provides substantially similar in-vitro metformin release for 30 days.

Example 2

| Ingredients | Quantity (mg/mL) |
|---|---|
| Core | |
| Metformin hydrochloride | 100.00 |
| Microcrystalline cellulose spheres | 90.00 |
| Hydroxypropylmethyl cellulose | 5.00 |
| Purified water | q.s. |
| Extended Release Coating | |
| Ethyl cellulose | 61.42 |
| Dibutyl sebacate | 6.82 |
| Acetone | q.s. |
| Purified water | q.s. |
| Total Weight of Extended Release Beads | 263.24 mg |
| Xylitol | 450.00 |
| Xanthan gum | 1.50 |
| Microcrystalline cellulose - sodium carboxymethyl cellulose (Avicel ® CL 611) | 20.00 |
| Strawberry flavor | 1.50 |
| Vehicle | |
| Purified water | q.s. to 1 mL |

Procedure:

1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Xylitol, xanthan gum, microcrystalline cellulose-sodium carboxymethyl cellulose, and strawberry flavor were mixed with the coated beads of step 4 to obtain a powder for suspension.
6. The powder for suspension as per step 5 is reconstituted with required amount of purified water when required to obtain the extended release suspension composition.

Example 3

| Ingredients | Quantity (mg/5 mL) |
|---|---|
| Core | |
| Metformin hydrochloride | 500.00 |
| Microcrystalline cellulose spheres | 375.00 |
| Hydroxypropylmethyl cellulose | 25.00 |
| Purified water | q.s. |
| Extended Release Coating | |
| Ethyl cellulose | 340.20 |
| Dibutyl sebacate | 37.80 |
| Acetone | q.s. |
| Purified water | q.s. |
| | |
| Total Weight of Extended Release Beads | 1278.00 mg |
| Xylitol | 2250.00 |
| Xanthan gum | 7.50 |
| Microcrystalline cellulose - sodium carboxymethyl cellulose (Avicel® RC 591) | 100.00 |
| Strawberry flavor | 7.50 |
| Vehicle | |
| Purified water | q.s. to 5 mL |

Procedure:
1. Metformin hydrochloride, microcrystalline cellulose, and hydroxypropylmethyl cellulose were sifted and mixed to obtain a blend.
2. The blend of step 1 was mixed with purified water to obtain a wet mass.
3. The wet mass of step 2 was extruded through an extruder.
4. The extrudates of step 3 were spherionized through a spherionizer to obtain beads.
5. The beads of step 4 were dried.
6. Ethyl cellulose and dibutyl sebacate were dispersed in a mixture of acetone and purified water.
7. The dried beads of step 5 were coated with the coating dispersion of step 6 to obtain a powder for suspension.
8. Xyltiol, xanthan gum, microcrystalline cellulose-sodium carboxymethyl cellulose, and strawberry flavor were dispersed in purified water to obtain the vehicle.
9. The powder for suspension of step 7 is reconstituted with the vehicle of step 8 when required to obtain the extended release suspension composition.

Example 4

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 45.00 |
| Dibutyl sebacate | 1.50 |
| Acetone | q.s. |
| Purified water | q.s. |
| | |
| Total Weight of Extended Release Beads | 186.50 mg |
| Metformin hydrochloride | 20.00 |
| Xylitol | 450.00 |
| Microcrystalline cellulose - sodium carboxymethyl cellulose (Avicel® CL-611) | 20.00 |
| Xanthan gum | 1.50 |
| Strawberry flavor | 2.00 |
| Sucralose | 0.50 |
| Sodium benzoate | 3.00 |
| Colloidal silicon dioxide | 3.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose-sodium carboxymethyl cellulose, xanthan gum, strawberry flavor, sucralose, sodium benzoate, and colloidal silicon dioxide were mixed.
6. The coated beads of step 4 were mixed with the mixture of step 5 to obtain a powder for suspension.
7. The powder for suspension of step 6 is reconstituted with required amount of purified water when required to form the extended release suspension composition.

In-Vitro Studies

The extended release suspension composition prepared according to Example 4 was stored at room temperature for 66 days. This extended release suspension was analyzed for the in-vitro dissolution at 0, 30, and 66 days using USP type II apparatus at 100 rpm, in 1000 mL of phosphate buffer with pH 6.8 at 37° C. The results of the release studies are represented in Table 2.

TABLE 2

Percentage (%) of the In-Vitro Metformin Release in USP Type II Apparatus (Media: Phosphate Buffer, pH 6.8, 1000 mL, and 100 rpm)

| | Number of Days | | |
|---|---|---|---|
| | 0 | 30 | 66 |
| Time (hours) | Percentage of Metformin Release | | |
| 0.5 | 27.0 | 25.6 | 26.3 |
| 1 | 30.9 | 31.5 | 31.6 |
| 2 | 56.9 | 58.3 | 50.9 |
| 3 | 74.9 | 72.8 | 70.6 |
| 4 | 85.6 | 81.7 | 81.6 |
| 5 | 89.1 | 87.7 | 87.4 |
| 6 | 94.9 | 90.3 | 92.3 |
| 8 | 97.7 | 93.5 | — |
| 10 | 99.4 | 95.3 | — |
| 12 | 103.4 | 99.4 | 100.0 |

From the above data, it is clear that the extended release suspension composition prepared according to Example 4 provides substantially similar in-vitro metformin release for 66 days.

The powder for suspension prepared as per Example 4 (till step 6) was kept for one month at accelerated conditions i.e., 40° C./75% R.H. After one month, the powder for suspension was reconstituted with required amount of purified water and this extended release suspension composition was kept for 66 days at room temperature. The in-vitro dissolution was determined at 0, 36, and 66 days using USP type II apparatus at 100 rpm, in 1000 mL of phosphate buffer with pH 6.8 at 37° C. The results of the release studies are represented in Table 3.

TABLE 3

Percentage (%) of the In-Vitro Metformin Release in USP Type II Apparatus (Media: Phosphate Buffer, pH 6.8, 1000 mL, and 100 rpm)

| Time (hours) | Number of Days After Reconstitution | | |
|---|---|---|---|
| | 0 | 36 | 66 |
| | Percentage of Metformin Release | | |
| 0.5 | 28.8 | 26.2 | 27.0 |
| 1 | 32.4 | 33 | 32.0 |
| 2 | 57.6 | 50.5 | 53.0 |
| 3 | 74.8 | 70.3 | 67.0 |
| 4 | 83.1 | 80.7 | 83.0 |
| 5 | 89.2 | 85.9 | 87.0 |
| 6 | 91.3 | 91.2 | 92.0 |
| 8 | 95.2 | — | 95.00 |
| 10 | 96.6 | — | 97.0 |
| 12 | 98.6 | 101.3 | 100.0 |

From the above data, it is clear that the extended release powder prepared according to Example 4 stored at accelerated conditions for one month, upon reconstitution and storage for 66 days at room temperature provides substantially similar in-vitro metformin release for 66 days. The results are shown in FIG. 1.

Example 5

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 50.40 |
| Dibutyl sebacate | 5.60 |
| Acetone | q.s. |
| Purified water | q.s. |
| Total Weight of Extended Release Beads | 196.00 mg |
| Metformin hydrochloride | 20.00 |
| Xylitol | 450.00 |
| Microcrystalline cellulose - sodium carboxymethyl cellulose (Avicel® CL-611) | 20.00 |
| Xanthan gum | 1.50 |
| Strawberry flavor | 2.00 |
| Sucralose | 0.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose-sodium carboxymethyl cellulose, xanthan gum, strawberry flavor, and sucralose were mixed.
6. The coated beads of step 4 were mixed with the mixture of step 5 to form a powder for suspension.
7. The powder for suspension of step 6 is reconstituted with required amount of purified water when required to form the extended release suspension composition.

In-Vitro Studies

The extended release suspension composition prepared as per Example 5 was stored at room temperature for 30 days. The in-vitro dissolution was determined at 0 and 30 days using USP type II apparatus at 100 rpm, in 1000 mL of phosphate buffer with pH 6.8 at 37° C. The results of the release studies are represented in Table 4.

TABLE 4

Percentage (%) of the In-Vitro Metformin Release in USP Type II Apparatus (Media: Phosphate Buffer, pH 6.8, 1000 mL, and 100 rpm)

| Time (hours) | Number of Days | |
|---|---|---|
| | 0 | 30 |
| | Percentage of Metformin Release | |
| 0.5 | 22 | 24 |
| 1 | 31 | 34 |
| 2 | 58 | 61 |
| 4 | 83 | 89 |
| 5 | 86 | 93 |
| 6 | 91 | 96 |
| 8 | 95 | 101 |
| 10 | 97 | 102 |
| 12 | 99 | 103 |

From the above data, it is clear that the extended release suspension composition prepared according to Example 5 provides substantially similar in-vitro metformin release for 30 days.

The powder for suspension prepared as per Example 5 (till step 6) was kept for three months at accelerated conditions i.e., 40° C./75% R.H. After three months, the powder for suspension was reconstituted with required amount of purified water and this extended release suspensions composition was kept for 32 days at room temperature. The in-vitro dissolution was determined at 0 and 32 days using USP type II apparatus at 100 rpm, in 1000 mL of phosphate buffer with pH 6.8 at 37° C. The results of the release studies are represented in Table 5.

TABLE 5

Percentage (%) of the In-Vitro Metformin Release in USP Type II Apparatus (Media: Phosphate Buffer, pH 6.8, 1000 mL, and 100 rpm)

| Time (hours) | Number of Days After Reconstitution | |
|---|---|---|
| | 0 | 32 |
| | Percentage of Metformin Release | |
| 0.5 | 22 | 26 |
| 1 | 33 | 37 |
| 2 | 60 | 66 |
| 4 | 85 | 90 |
| 5 | 89 | 94 |
| 6 | 92 | 97 |
| 8 | 96 | 101 |
| 10 | 98 | 103 |
| 12 | 101 | 103 |

The powder for suspension prepared as per Example 5 (till step 6) was kept for six months at accelerated conditions i.e., 40° C./75% R.H. After six months, the powder for suspension was reconstituted with required amount of purified water and this extended release suspensions composition was kept for 32 days at room temperature. The in-vitro dissolution was determined at 0 and 32 days using USP type II apparatus at 100 rpm, in 1000 mL of phosphate buffer with pH 6.8 at 37° C. The results of the release studies are represented in Table 6.

TABLE 6

Percentage (%) of the In-Vitro Metformin Release in USP Type II Apparatus (Media: Phosphate Buffer, pH 6.8, 1000 mL, and 100 rpm)

| Time (hours) | Number of Days After Reconstitution | |
|---|---|---|
| | 0 | 32 |
| | Percentage of Metformin Release | |
| 0.5 | 24 | 25 |
| 1 | 35 | 34 |
| 2 | 63 | 60 |
| 4 | 87 | 86 |
| 5 | 91 | 91 |
| 6 | 94 | 94 |
| 8 | 97 | 98 |
| 10 | 99 | 101 |
| 12 | 99 | 101 |

Figure 2:
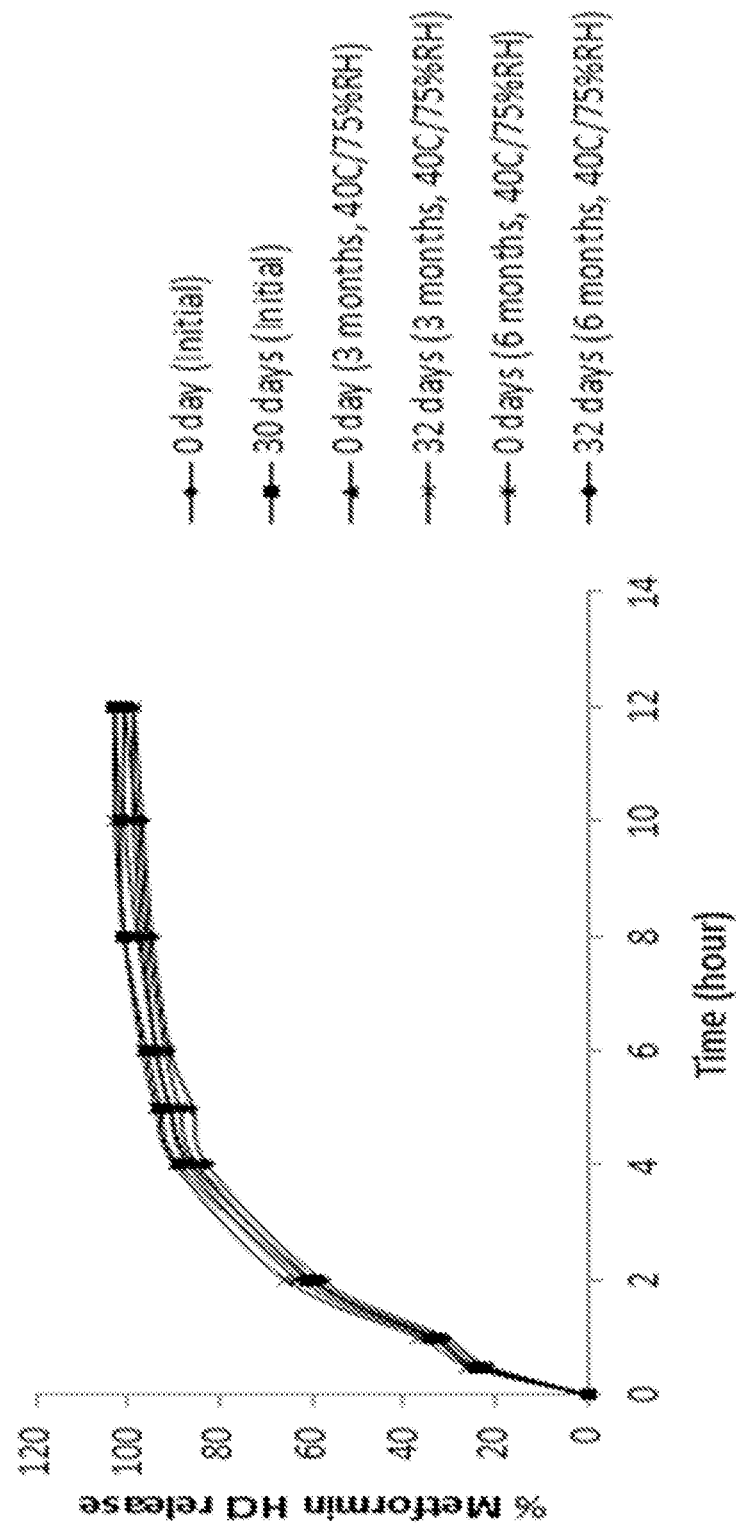
FIG. 2 shows the in-vitro dissolution release on day 0 and day 30 of the extended release suspension composition prepared according to Example 5 upon storage at room temperature. This figure also shows the in-vitro dissolution release on day 0 and day 32 of the extended release suspension composition (at room temperature) formed after reconstituting the powder stored for three months and six months at accelerated conditions.

From the above data, it is clear that the extended release powder prepared according to Example 5 stored at accelerated conditions for three or six months, upon reconstitution and storage for 32 days at room temperature provides substantially similar in-vitro metformin release for 32 days. The results are presented in FIG. 2.

Example 6

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 61.48 |
| Dibutyl sebacate | 1.52 |
| Acetone | q.s. |
| Purified water | q.s. |
| Total Weight of Extended Release Beads | 203.00 mg |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Strawberry flavor | 2.00 |
| Sucralose | 0.50 |
| Colloidal silicon dioxide | 3.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose-sodium carboxymethyl cellulose, xanthan gum, strawberry flavor, sucralose, and colloidal silicon dioxide were mixed.
6. The coated beads of step 4 were mixed with the mixture of step 5 to form a powder for suspension.
7. The powder for suspension of step 6 is reconstituted with required amount of purified water when required to form the extended release suspension composition.

In-Vitro Studies

The extended release suspension composition prepared as per Example 6 was stored at room temperature for 30 days. The in-vitro dissolution was determined at 0 and 30 days using USP type II apparatus at 100 rpm, in 1000 mL of phosphate buffer with pH 6.8 at 37° C. The results of the release studies are represented in Table 7.

TABLE 7

Percentage (%) of the In-Vitro Metformin Release in USP Type II Apparatus (Media: Phosphate Buffer, pH 6.8, 1000 mL, and 100 rpm)

| Number of Days Time (hours) | 0 | 30 |
|---|---|---|
| | Percentage of Metformin Release | |
| 0.5 | 20 | 22 |
| 1 | 27 | 28 |
| 2 | 59 | 64 |
| 3 | 77 | 80 |
| 4 | 84 | 89 |
| 5 | 88 | 93 |
| 6 | 92 | 95 |
| 8 | 95 | 99 |
| 10 | 97 | 101 |
| 12 | 98 | 103 |

From the above in-vitro release data, it is evident that the extended release suspension composition prepared according to Example 6 provides the substantially similar in-vitro metformin release for 30 days.

The powder for suspension prepared as per Example 6 (till step 6) was kept for one month at accelerated conditions i.e., 40° C./75% R.H. After one month, the powder for suspension was reconstituted with required amount of purified water and this extended release suspension composition was kept for 30 days at room temperature. The in-vitro dissolution was determined at 0 and 30 days using USP type II apparatus at 100 rpm, in 1000 mL of phosphate buffer with pH 6.8 at 37° C. The results of the release studies are represented in Table 8.

TABLE 8

Percentage (%) of the In-Vitro Metformin Release in USP Type II Apparatus (Media: Phosphate Buffer, pH 6.8, 1000 mL, and 100 rpm)

| Number of Days After Reconstitution Time (hours) | 0 | 30 |
|---|---|---|
| | Percentage of Metformin Release | |
| 0.5 | 20 | 19 |
| 1 | 26 | 26 |
| 2 | 57 | 57 |
| 3 | 74 | 74 |
| 4 | 82 | 80 |
| 5 | 86 | 85 |
| 6 | 90 | 88 |

TABLE 8-continued

Percentage (%) of the In-Vitro Metformin Release in USP Type II Apparatus (Media: Phosphate Buffer, pH 6.8, 1000 mL, and 100 rpm)

| Number of Days After Reconstitution Time (hours) | 0 | 30 |
|---|---|---|
| | Percentage of Metformin Release | |
| 8 | 92 | 91 |
| 10 | 94 | 93 |
| 12 | 96 | 94 |

Figure 3:
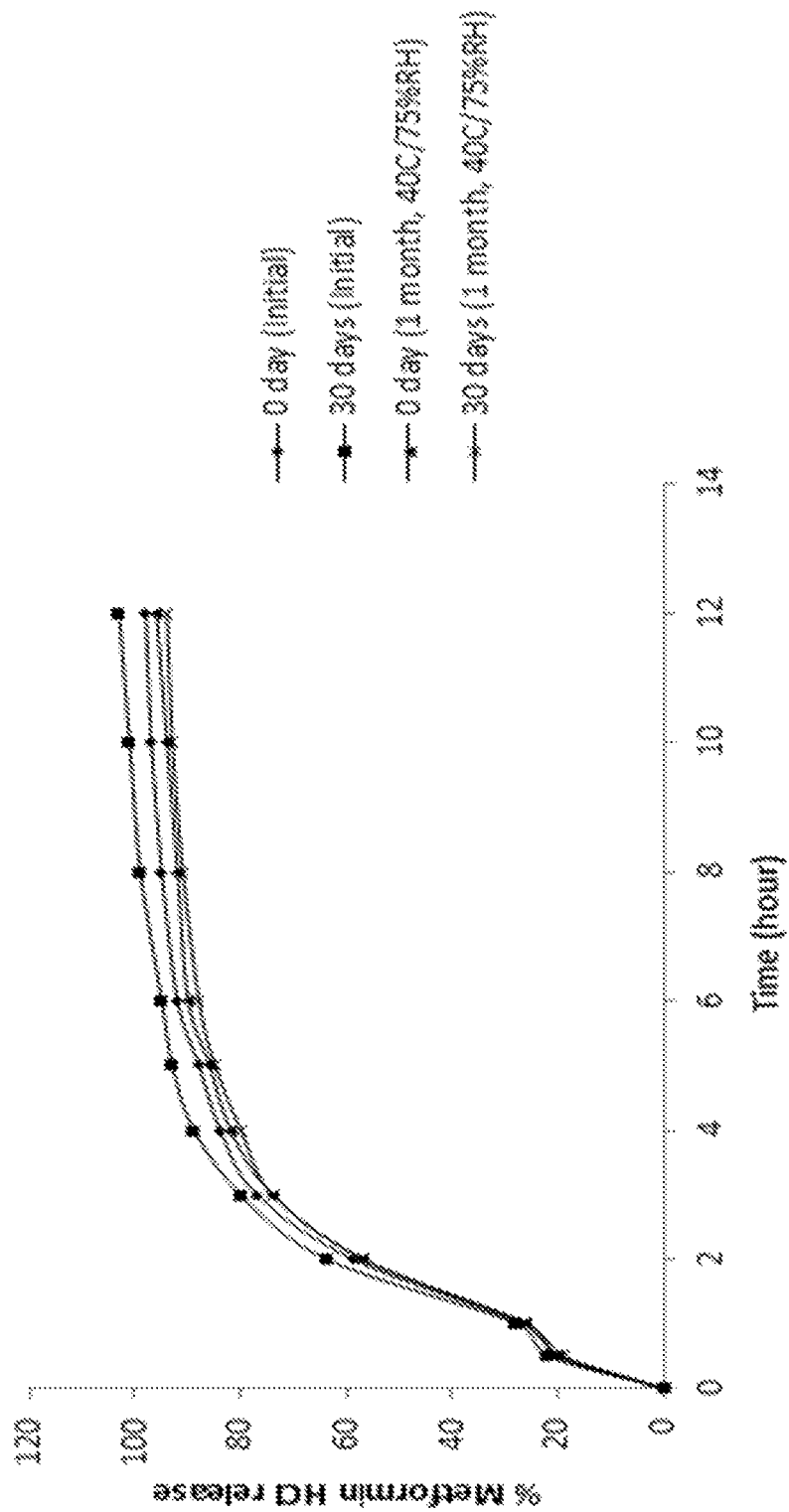
FIG. 3 shows the in-vitro dissolution release on day 0 and day 30 of the extended release suspension composition prepared according to Example 6 upon storage at room temperature. This figure also shows the in-vitro dissolution release on day 0 and day 30 of the extended release suspension composition (at room temperature) formed after reconstituting the powder stored for one month at accelerated conditions.

From the above data, it is clear that the extended release powder prepared according to Example 6 stored at accelerated condition for one month, upon reconstitution and storage for 30 days at room temperature provides substantially similar in-vitro metformin release for 30 days. The results are presented in FIG. 3.

Osmolality Measurement of the Extended Release Suspension

The metformin extended release powder prepared according to the Example 6 (till step 6) was reconstituted with required amount of purified water. This suspension was shaken manually for at least 20 minutes. This suspension was then filtered and diluted with purified water and the osmolality was measured using Osmomat® 030-D.

The osmolality of the suspension base was found to be 4.112 osmol/kg of the suspension base on day 0.

The osmolality of the suspension base was found to be 4.328 osmol/kg of the suspension base on day 7.

It is evident from the above data that the osmolality of the suspension base of the extended release suspension composition as per Example 6 remains equivalent for seven days.

Osmolality Measurement of the External Phase

The metformin hydrochloride, xylitol, microcrystalline cellulose-sodium carboxymethyl cellulose, xanthan gum, strawberry flavor, sucralose, and colloidal silicon dioxide were mixed as per step 5 of Example 6. This mixture was reconstituted with required amount of purified water. This suspension was then filtered and diluted with purified water, and the osmolality was measured using Osmomat® 030-D.

The osmolality of the suspension base i.e., external phase was found to be 4.204 osmol/kg of the suspension base.

Osmolality Measurement of the Internal Phase

Various solutions having various concentrations of osmogent (sodium chloride) were prepared as per Examples 6A-6F. The osmolalities of these solutions were measured using Osmomat® 030-D.

| Ingredient | Example 6A | Example 6B | Example 6C | Example 6D | Example 6E | Example 6F |
|---|---|---|---|---|---|---|
| Sodium Chloride (mg) | 30.00 | 60.00 | 120.00 | 180.00 | 240.00 | 300.00 |
| Purified water | q.s. to 1 mL | q.s. to 1 mL | q.s. to 1 mL | q.s. to 7.5 mL | q.s. to 1 mL | q.s. to 1 mL |
| Osmolality (osmol/kg) | 0.910 | 1.787 | 3.574* | 5.361* | 7.148* | 8.935* |

*Extrapolated using values of dilute solutions

The coated beads of step 4 were dispersed in different solutions as per Examples 6A-6F. These solutions were kept for seven days at room temperature. After seven days, each solution was analyzed by HPLC for metformin content. The results are represented in following Table 9.

TABLE 9

Effect of Osmolality on Metformin Leaching

| Example | Osmolality (osmol/kg) of the solution | Metformin Content (%) |
|---|---|---|
| 6A | 0.910 | 67.3 |
| 6B | 1.787 | 30.3 |
| 6C | 3.574* | 2.9 |
| 6D | 5.361* | 1.8 |
| 6E | 7.148* | 1.7 |
| 6F | 8.935* | 1.0 |

*Extrapolated using values of dilute solutions

From the above data, it is evident that the leaching of metformin from the coated beads into the solution was decreasing as the osmolality of the solution was increasing from Examples 6A-6F. The leaching is found to be significantly reduced from Example 6C onwards. The osmolality of Example 6C i.e., 3.574 is considered as osmolality of the internal phase.

Osmolality Ratio 1.176

Dose Uniformity Data

The extended release suspension equivalent to 100 mL was prepared according to formula given in Example 6. This suspension was shaken manually for at least 20 minutes and then ten 7.5 mL samples were taken with a graduated syringe. The metformin content of each sample is determined by HPLC method [Inertsil ODS column (250×4.6 mm, 5 µm); mobile phase-buffer (pH 3.5):acetonitrile (95:5 v/v); flow rate of 1.5 mL/min; UV detection at 233 nm] The results are shown in Table 10.

TABLE 10

Metformin Content (% w/w) For Each 7.5 mL of Suspension

| Sample Number | Metformin content (%) for each 7.5 mL of suspension |
|---|---|
| 1 | 98.6 |
| 2 | 97.9 |
| 3 | 96.6 |
| 4 | 97.2 |
| 5 | 99.7 |
| 6 | 96.4 |
| 7 | 95.9 |
| 8 | 97.3 |
| 9 | 98.8 |
| 10 | 96.9 |
| Mean value | 97.5 |

From the above data, it is evident that the extended release suspension composition prepared as per Example 6 is homogeneous.

Assay Data

The assay for the extended release suspension composition prepared as per Example 6 was determined at 0 day and after storage at room temperature for 30 days. The powder for suspension prepared as per Example 6 (till step 6) was kept for one month at 40° C./75% R.H. After one month, the powder for suspension was reconstituted with required amount of purified water and then assay was determined at 0 day and after storage at room temperature for 30 days. The assay of metformin was determined by HPLC method [Inertsil ODS column (250×4.6 mm, 5 µm); mobile phase-buffer (pH 3.5):acetonitrile (95:5 v/v); flow rate of 1.5 mL/min; UV detection at 233 nm]. The results are shown in Table 11.

TABLE 11

Assay for Metformin

| Condition | Assay (%) for metformin | |
|---|---|---|
| | 0 day | 30 days |
| Initial | 97.0 | 99.5 |
| 1 month (40° C./75% R.H) | 97.4 | 98.9 |

It is evident from the above data that the extended release suspension composition prepared as per Example 6 is stable.

Example 7

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 68.31 |
| Dibutyl sebacate | 1.69 |
| Acetone | q.s. |
| Purified water | q.s. |
| Total Weight of Extended Release Beads | 210.00 mg |
| Suspension base | |
| Metformin hydrochloride | 20.00 |
| Xylitol | 450.00 |
| Microcrystalline cellulose-sodium carboxymethyl cellulose (Avicel ® CL-611) | 20.00 |
| Xanthan gum | 1.50 |
| Methyl paraben | 1.80 |
| Propyl paraben | 0.20 |
| Strawberry flavor | 2.00 |
| Sucralose | 0.50 |
| Colloidal silicon dioxide | 3.50 |
| Purified water | 472.00 mg |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3 and dried to form a powder for suspension.
5. Purified water was heated to dissolve methyl paraben and propyl paraben.
6. Metformin hydrochloride, xylitol, microcrystalline cellulose-sodium carboxymethyl cellulose, xanthan gum, strawberry flavor, sucralose, and colloidal silicon dioxide were mixed in the solution of step 5 to form a suspension base.
7. The powder for suspension of step 4 was prefilled in the second chamber of a dual-chamber pack.
8. The suspension base of step 7 was prefilled in a container of a first chamber of a dual-chamber pack.
9. The two chambers were assembled and the pack was activated to form the extended release suspension composition when required.

In-Vitro Studies

The extended release suspension composition prepared as per Example 7 (for a dose equivalent to 750 mg of metformin hydrochloride) was stored at room temperature for 120 days. The in-vitro dissolution was determined at 0, 45, 90, and 120 days using USP type II apparatus at 100 rpm, in 1000 mL of phosphate buffer with pH 6.8 at 37° C. The results of the release studies are represented in Table 12.

TABLE 12

Percentage (%) of the In-Vitro Metformin Release in USP Type II Apparatus (Media: Phosphate Buffer, pH 6.8, 1000 mL, and 100 rpm)

| Number of Days | 0 | 45 | 90 | 120 |
|---|---|---|---|---|
| Time (hours) | Percentage of Metformin Release | | | |
| 0.5 | 20 | 21 | 20 | 21 |
| 1 | 27 | 25 | 27 | 25 |
| 2 | 55 | 52 | 55 | 52 |
| 3 | 74 | 72 | 74 | 72 |
| 4 | 83 | 81 | 83 | 81 |
| 5 | 85 | 86 | 85 | 86 |
| 6 | 87 | 90 | 87 | 90 |
| 8 | 91 | 94 | 91 | 94 |
| 10 | 93 | 96 | 93 | 96 |
| 12 | 94 | 97 | 94 | 97 |

From the above in-vitro release data, it is evident that the extended release suspension composition prepared according to Example 7 provides the substantially similar in-vitro metformin release for 120 days.

The dual-chamber pack was kept for 1 month at accelerated conditions i.e., 40° C./75% R.H. After 1 month, the pack was activated to form an extended release suspension composition which was kept for 120 days at room temperature. The in-vitro dissolution was determined at 0, 45, 90, and 120 days using USP type II apparatus at 100 rpm, in 1000 mL of phosphate buffer with pH 6.8 at 37° C. The results of the release studies are represented in Table 13.

TABLE 13

Percentage (%) of the In-Vitro Metformin Release in USP Type II Apparatus (Media: Phosphate Buffer, pH 6.8, 1000 mL, and 100 rpm)

| Number of Days | 0 | 45 | 90 | 120 |
|---|---|---|---|---|
| Time (hours) | Percentage of Metformin Release | | | |
| 0.5 | 21 | 21 | 21 | 20 |
| 1 | 27 | 25 | 26 | 26 |
| 2 | 56 | 55 | 52 | 54 |
| 3 | 74 | 74 | 76 | 72 |
| 4 | 83 | 81 | 82 | 81 |
| 10 | 96 | 96 | 97 | 94 |

The dual-chamber pack was kept for 3 months at accelerated conditions i.e., 40° C./75% R.H. After 3 months, the pack was activated to form an extended release liquid composition which was kept for 45 days at room temperature. The in-vitro dissolution was determined at 0 and 45 days using USP type II apparatus at 100 rpm, in 1000 mL of phosphate buffer with pH 6.8 at 37° C. The results of the release studies are represented in Table 14.

TABLE 14

Percentage (%) of the In-Vitro Metformin Release in USP Type II Apparatus (Media: Phosphate Buffer, pH 6.8, 1000 mL, and 100 rpm)

| Number of Days | 0 | 45 |
|---|---|---|
| Time (hours) | Percentage of Metformin Release | |
| 0.5 | 21 | 21 |
| 1 | 26 | 25 |
| 2 | 55 | 53 |
| 3 | 75 | 72 |
| 4 | 80 | 80 |
| 10 | 95 | 92 |

From the above data, it is clear that the powder for suspension and suspension base stored in the dual-chamber pack of the instant invention at accelerated conditions for 1 month and 3 months, upon activation of the pack forms extended release suspension compositions which when stored for 120 days and 45 days respectively at room temperature provides substantially similar in-vitro metformin release.

Stability Data

The related substances for the extended release suspension composition prepared as per Example 7 were determined at 0 day and after storage at room temperature for 45 and 120 days. The powder for suspension and suspension base was stored in the dual-chamber pack for one month and for three months at 40° C./75% R.H. After one month or three months, the pack was activated to form an extended release suspension composition and then related substances were determined at 0 day and after storage at room temperature for 45 days and 120 days.

The assay of metformin was determined by HPLC method. The results are shown in Table 15.

TABLE 15

Stability Data for Metformin

| Related Substances (% w/w) | Initial | | | 1 month (40° C./75% R.H) | | | 3 month (40° C./75% R.H) | |
|---|---|---|---|---|---|---|---|---|
| | 0 day | 45 days | 120 days | 0 day | 45 days | 120 days | 0 day | 45 days |
| Cyanoguai-nidine | BLQ | 0.001 | 0.00072 | 0.001 | 0.001 | 0.001 | 0.001 | 0.001 |
| Highest unknown impurity | 0.05 | 0.05 | 0.04 | 0.05 | 0.04 | 0.04 | 0.05 | 0.04 |
| Total impurities | 0.05 | 0.05 | 0.04 | 0.05 | 0.04 | 0.04 | 0.09 | 0.04 |

*BLQ: Below limit of Quantification

Osmolality of the Suspension Base:

3.960 osmol/Kg of the suspension base as measured by using Osmomat® 030-D.

Viscosity of the Suspension Base:

2880 cps as measured by using Brookfield Viscometer using a #2 spindle rotating at 5 rpm at 25° C.

Example 8

Preparation of Extended Release Beads

| Ingredients | Quantity (mg) |
|---|---|
| Core | |
| Guanfacine hydrochloride | 1.15 |
| Microcrystalline cellulose spheres | 4.00 |
| Hydroxypropylmethyl cellulose | 30.00 |
| Mannitol | 10.00 |
| Purified Water | q.s. |
| Extended Release Coating | |
| Ethyl cellulose | 14.22 |
| Dibutyl sebacate | 1.58 |
| Acetone | q.s. |
| Purified Water | q.s. |
| Total Weight of Extended Release Beads | 60.95 mg |

Procedure:
1. Guanfacine hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.

Various solutions having various concentrations of osmogent (sodium chloride) were prepared as per Examples 8A-7D. The osmolalities of these solutions were measured using Osmomat® 030-D.

| Ingredient | Example 8A | Example 8B | Example 8C | Example 8D |
|---|---|---|---|---|
| Sodium Chloride (mg) | 30.00 | 60.00 | 120.00 | 180.00 |
| Purified water | q.s. to 1 mL | q.s. to 1 mL | q.s. to 1 mL | q.s. to 1 mL |
| Osmolality (osmol/kg) | 0.910 | 1.787 | 3.574* | 5.361* |

*Extrapolated using values of dilute solutions

Sodium chloride was dissolved in purified water as per Examples 8A-8D. The osmolality of these solutions were measured using Osmomat® 030-D.

The coated beads of step 4 were dispersed in different suspension bases as per Examples 8A-8D. These suspensions were kept for seven days at room temperature. After seven days, each suspension was filtered and diluted with purified water. These were then analyzed by using HPLC for guanfacine content. The results are represented in following Table 16.

TABLE 16

Effect of Osmolality on Guanfacine Leaching

| Example | Osmolality (osmol/kg) of the solution | Guanfacine Content (%) |
|---|---|---|
| 8A | 0.910 | 69.80 |
| 8B | 1.787 | 8.90 |
| 8C | 3.574* | 1.30 |
| 8D | 5.361* | 0.30 |

*Extrapolated using values of dilute solutions

From the above data, it is evident that the leaching of guanfacine from the coated beads into the solution was decreasing as the osmolality of the solution was increasing from Examples 8A-8D.

Example 9

| Ingredients | Quantity (mg/mL) |
| --- | --- |
| Core | |
| Valacyclovir hydrochloride (equivalent to 100 mg of valacyclovir) | 111.24 |
| Microcrystalline cellulose spheres | 70.00 |
| Hydroxypropylmethyl cellulose | 5.56 |
| Purified water | q.s. |
| Extended Release Coating | |
| Ethyl cellulose | 45.58 |
| Dibutyl sebacate | 1.13 |
| Acetone | q.s. |
| Purified water | q.s. |
| Total Weight of Extended Release Beads | 233.51 mg |
| Xylitol | 450.00 |
| Xanthan gum | 1.50 |
| Microcrystalline cellulose-sodium carboxymethyl cellulose (Avice ® CL 611) | 20.00 |
| Strawberry flavor | 1.50 |
| Vehicle | |
| Purified water | q.s to 1.0 ml |

Procedure:
1. Valacyclovir hydrochloride and hydroxypropylmethyl cellulose are dissolved in purified water.
2. Microcrystalline cellulose spheres are coated with the solution of step 1.
3. Ethyl cellulose and dibutyl sebacate are dispersed in a mixture of acetone and purified water.
4. The beads of step 2 are coated with the coating dispersion of step 3.
5. Xylitol, xanthan gum, microcrystalline cellulose-sodium carboxymethyl cellulose, strawberry flavor are mixed.
6. The coated beads of step 4 are mixed with the mixture of step 5 to form a powder for suspension.
7. The powder for suspension of step 6 is reconstituted with required amount of purified water when required to form the extended release suspension composition.

Example 10

| Ingredients | Quantity (mg/5 mL) |
| --- | --- |
| Core | |
| Amoxicillin | 1000.00 |
| Microcrystalline cellulose spheres | 200.00 |
| Polyvinylpyrrolidone | 60.00 |
| Purified water | q.s. |
| Extended Release Coating | |
| Ethyl cellulose | 500.00 |
| Dibutyl sebacate | 50.00 |
| Acetone | q.s. |
| Purified water | q.s. |
| Total Weight of Extended Release Beads | 1810.00 mg |
| Clavulanic acid | 62.50 |
| Lemon flavor | 1.50 |
| Xylitol | 450.00 |
| Microcrystalline cellulose-sodium carboxymethyl cellulose (Avicel ® CL 611) | 20.00 |
| Strawberry flavor | 1.50 |
| Vehicle | |
| Purified water | q.s to 5.0 mL |

Procedure:
1. Amoxicillin and polyvinylpyrrolidone are dispersed in purified water.
2. Microcrystalline cellulose spheres are coated with the solution of step 1.
3. Ethyl cellulose and dibutyl sebacate are dispersed in a mixture of acetone and purified water.
4. The beads of step 2 are coated with the coating dispersion of step 3.
5. Clavulanic acid, lemon flavor, xylitol, microcrystalline cellulose-sodium carboxymethyl cellulose, strawberry flavor are mixed.
6. The coated beads of step 4 are mixed with the mixture of step 5 to form a powder for suspension.
7. The powder for suspension of step 6 is reconstituted with required amount of purified water when required to form the extended release suspension composition.

Example 11

| Ingredients | Quantity (mg/mL) |
| --- | --- |
| Core | |
| Esomeprazole magnesium | 44.50 |
| Non-pareil seeds | 100.00 |
| Hydroxypropyl cellulose | 20.00 |
| Crospovidone | 30.00 |
| Purified water | q.s. |
| Seal Coating | |
| Hydroxypropyl methyl cellulose | 14.98 |
| Polyethylene glycol | 1.49 |
| Talc | 2.98 |
| Purified water | q.s. |
| Extended Release Coating | |
| Methacrylic acid copolymer dispersion (Eudragit ® L30 D-55) | 33.47 |
| Polyethylene glycol | 3.35 |
| Talc | 12.72 |
| Titanium dioxide | 3.95 |
| Purified water | q.s. |
| Lubrication | |
| Talc | 12.56 |
| Total Weight of Extended Release Beads | 280.00 mg |
| Xylitol | 450.00 |
| Vehicle | |
| Purified water | q.s to 1.0 mL |

Procedure:
1. Esomeprazole magnesium, hydroxypropyl cellulose, crospovidone are dispersed in purified water and is stirred to get form a dispersion.
2. The non-pareil seeds are coated with dispersion of step 1.
3. The hydroxypropylmethyl cellulose, polyethylene glycol, and talc are dispersed in purified water to get a dispersion.

4. The coated pellets of step 2 are coated with the dispersion of step 3.
5. The polyethylene glycol, methacrylic acid copolymer dispersion, talc, and titanium dioxide are dispersed in purified water to get a dispersion.
6. The coated pellets of step 4 are coated with the dispersion of step 5.
7. The coated pellets of step 6 are lubricated with talc.
8. The lubricated pellets of step 7 are mixed with xylitol to obtain a powder for suspension.
9. The powder for suspension of step 8 is reconstituted with required amount of purified water when required to form the extended release suspension composition.

We claim:

1. A stable extended release reconstituted powder for suspension composition comprising multiple coated cores of an active ingredient, wherein upon reconstitution with a suspension base, the composition ensures substantially similar in-vitro dissolution release profile of the active ingredient upon storage of the composition upon reconstitution for at least seven days; and wherein the active ingredient is not bound to an ion-exchange matrix; and wherein the suspension base used for reconstitution of the composition is characterized by having the features of:
   (i) a viscosity in a range of about 500 cps to about 15,000 cps and
   (ii) an osmolality of at least 1 osmol/kg of the suspension base;
   wherein the composition upon reconstitution is characterized by having an osmolality ratio of at least about 1, the osmolality ratio being the ratio of the osmolality of the external phase to the osmolality of the internal phase, the external phase being the suspension base without multiple coated cores of the active ingredient and the internal phase being the coated cores of the active ingredient;
   wherein the osmolality of the internal phase is the osmolality of a solution which prevents significant leaching of the active ingredient from the coated cores into the solution when the coated cores are suspended in said solution;
   significant leaching being more than 20% of the active ingredient is leached out from the coated cores into the solution:
   wherein the coated cores consist of a core of an active ingredient and a coating layer over said core comprising one or more release-controlling agents and average diameter of the coated cores ranges from about 150 μm to about 500 μm, and wherein the composition is homogeneous and the active ingredient is layered onto an inert particle to form the core.

2. The stable extended release reconstituted powder for suspension composition of claim 1, wherein the suspension base comprises:
   (i) a suspending agent;
   (ii) an osmogent; and
   (iii) an aqueous vehicle.

3. The stable extended release reconstituted powder for suspension composition of claim 1, wherein the inert particle is selected from the group consisting of a non-pareil seed, a microcrystalline cellulose sphere, a dibasic calcium phosphate bead, a mannitol bead, a silica bead, a tartaric acid pellet, and a wax based pellet.

4. The stable extended release reconstituted powder for suspension composition of claim 2, wherein the osmogent is selected from the group consisting of carbohydrates; water-soluble salts of inorganic acids; water-soluble salts of organic acids; water-soluble amino acids; urea or its derivatives; propylene glycol; glycerin; polyethylene oxide; xanthan gum; hydroxypropylmethyl cellulose; and mixtures thereof.

5. The stable extended release reconstituted powder for suspension composition of claim 2, wherein the suspending agent is selected from group consisting of cellulose derivatives; carbomers; gums; pectin; dextran; gelatin; polyethylene glycols; polyvinyl compounds; sugar alcohols; and mixtures thereof.

6. The stable extended release reconstituted powder for suspension composition of claim 1, wherein the release-controlling agent is selected from the group consisting of a pH-dependent release-controlling agent, a pH-independent release-controlling agent, and mixtures thereof.

7. The stable extended release reconstituted powder for suspension composition of claim 6, wherein the pH-dependent release-controlling agent is selected from the group consisting of acrylic copolymers; cellulose acetate phthalate; cellulose acetate succinates; hydroxyalkyl cellulose phthalates; hydroxyalkyl cellulose acetate succinates; vinyl acetate phthalates; vinyl acetate succinate; cellulose acetate trimelliate; polyvinyl derivatives; zein; shellac; and mixtures thereof.

8. The stable extended release reconstituted powder for suspension composition of claim 6, wherein the pH-independent release-controlling agent is selected from the group consisting of cellulosic polymers; acrylic copolymers; cellulose acetate; polyethylene derivatives; polyvinyl alcohol; polyvinyl acetate; gums; lipids; fatty acids or their salts/derivatives; a mixture of polyvinyl acetate and polyvinyl pyrrolidone; and mixtures thereof.

9. The stable extended release reconstituted powder for suspension composition of claim 1, wherein the active ingredient is selected from the group consisting of metformin, acarbose, miglitol, voglibose, repaglinide, nateglinide, glibenclamide, glimepride, glipizide, gliclazide, chloropropamide, tolbutamide, phenformin, aloglitin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, verapamil, albuterol, salmeterol, acebutolol, sotalol, penicillamine, norfloxacin, ciprofloxacin, ofloxacin, levofloxacin, moxifloxacin, cefpodoxime, tetracycline, demeclocycline hydrochloride, amoxicillin, clavulanate potassium, azithromycin, losartan, irbesartan, eprosartan, valsartan, diltiazem, isosorbide mononitrate, ranolazine, propafenone, hydroxyurea, hydrocodone, delavirdine, pentosan polysulfate, abacavir, amantadine, acyclovir, ganciclovir, valacyclovir, valganciclovir, saquinavir, indinavir, nelfinavir, lamivudine, didanosine, zidovudine, nabumetone, celecoxib, mefenamic acid, naproxen, propoxyphene, cimetidine, ranitidine, albendazole, mebendazole, thiobendazole, pyrazinamide, praziquantel, chlorpromazine, sumatriptan, bupropion, aminobenzoate, pyridostigmine bromide, potassium chloride, niacin, tocainide, quetiapine, fexofenadine, sertraline, chlorpheniramine, rifampin, methenamine, nefazodone, modafinil, metaxalone, morphine, sevelamer, lithium carbonate, flecainide acetate, simethicone, methyldopa, chlorthiazide, metyrosine, procainamide, entacapone, metoprolol, propanolol hydrochloride, chlorzoxazone, tolmetin, tramadol, bepridil, phenytoin, gabapentin, fluconazole, terbinafine, atorvastatin, doxepine, rifabutin, mesalamine, etidronate, nitrofurantoin, choline magnesium trisalicylate, theophylline, nizatidine, methocarbamol, mycophenolate mofetil, tolcapone, ticlopidine, capecitabine, orlistat, colsevelam, meperidine, hydroxychloroquine, guaifenesin, guanfacine, amiodarone, quinidine, atomoxetine, felbamate, pseudoephedrine, carisoprodol, venlafaxine, etodolac, chondrotin, lansoprazole, pantoprazole, esomeprazole, dexlansoprazole, dexmethylphenidate, methylphenidate, sodium oxybate, valproic acid or its salts, divalproex, topiramate, carbamazepine, oxcarbazepine, and isotretinoin.

10. The stable extended release reconstituted powder for suspension composition of claim 2, wherein the suspension base further comprises one or more pharmaceutically acceptable excipients selected from the group consisting of anti-caking agents, wetting agents, preservatives, buffering agents, flavoring agents, anti-oxidants, chelating agents, solubility enhancing agents, pH modifying agents, adsorbents, complexing agents, and combinations thereof.

* * * * *